(12) United States Patent
Zats et al.

(10) Patent No.: US 11,865,213 B2
(45) Date of Patent: Jan. 9, 2024

(54) SEMAGLUTIDE DEPOT SYSTEMS AND USE THEREOF

(71) Applicant: Mapi Pharma Ltd., Ness Ziona (IL)

(72) Inventors: Galina Zats, Rehovot (IL); Nadav Bleich Kimelman, Tel Aviv (IL); Shai Rubnov, Tel Aviv (IL); Ehud Marom, Tel Aviv (IL)

(73) Assignee: MAPI PHARMA LTD., Ness Ziona (IL)

( * ) Notice: Subject to any disclaimer, the term of this patent is extended or adjusted under 35 U.S.C. 154(b) by 0 days.

(21) Appl. No.: 17/534,533

(22) Filed: Nov. 24, 2021

(65) Prior Publication Data

US 2023/0014750 A1 Jan. 19, 2023

Related U.S. Application Data

(60) Provisional application No. 63/218,405, filed on Jul. 5, 2021.

(51) Int. Cl.
| | |
|---|---|
| *A61K 38/26* | (2006.01) |
| *A61K 9/14* | (2006.01) |
| *A61K 9/16* | (2006.01) |
| *A61P 3/04* | (2006.01) |
| *A61P 3/10* | (2006.01) |

(52) U.S. Cl.
CPC .......... *A61K 9/1647* (2013.01); *A61K 9/1611* (2013.01); *A61K 9/1635* (2013.01); *A61K 9/1682* (2013.01); *A61K 38/26* (2013.01); *A61P 3/04* (2018.01); *A61P 3/10* (2018.01)

(58) Field of Classification Search
None
See application file for complete search history.

(56) References Cited

U.S. PATENT DOCUMENTS

| | | | | |
|---|---|---|---|---|
| 2008/0044543 | A1* | 2/2008 | McClements | A23D 7/0053 426/573 |
| 2008/0220070 | A1* | 9/2008 | Fu | A61K 9/0017 514/6.6 |
| 2015/0190474 | A1* | 7/2015 | Jensen | A61K 38/26 514/4.9 |
| 2017/0281547 | A1* | 10/2017 | Karavas | A61K 9/0019 |
| 2019/0133952 | A1* | 5/2019 | Liu | A61K 9/1647 |
| 2020/0298196 | A1 | 9/2020 | Lee | |
| 2021/0283209 | A1 | 9/2021 | Marom | |

FOREIGN PATENT DOCUMENTS

| | | | | |
|---|---|---|---|---|
| CN | 110101846 | A | 8/2019 | |
| CN | 113018277 | * | 6/2021 | ............. A61K 38/26 |
| WO | 2011080733 | A1 | 7/2011 | |
| WO | WO 2017/186077 | * | 11/2017 | ............... A61K 9/16 |
| WO | WO 2018/075901 | * | 4/2018 | ............. A61K 38/26 |
| WO | 2018136909 | A1 | 7/2018 | |
| WO | 2020028907 | A1 | 2/2020 | |
| WO | 2020210764 | A1 | 10/2020 | |
| WO | 2021020885 | A1 | 2/2021 | |
| WO | 2021162532 | A2 | 8/2021 | |

OTHER PUBLICATIONS

Mao, S., et al. Int. J. Pharm. (2007), 334; 137-148.*
Zhang, J. X., et al. J. Microencapsul. (2005), 22(4); 413-422.*
Grieco, M., et al. Front. Neurosci. (2019), 13; Article 1112.*
Park, H., et al. Pharmaceutics (2019), 11(12); 627.*
Zhang, W., et al. Small (2019), 15(42); 1903087.*
Wang, Z. J. Appl. Polymer Sci. (2010), 115; 2599-2608.*
Zhang, J. X., et al. J. Microencapsul. (2004), 21(7); 775-785.*
Knudsen and Lau (2019) The Discovery and Development of Liraglutide and Semaglutide. Frontiers in Endocrinology (Lausanne) 10: 155; 32 pages.
Suzuki et al., (2020) Recent Developments in Therapeutic Peptides for the Glucagon-like Peptide 1 and 2 Receptors. J Med Chem 63(3): 905-927.
Yu et al., "Battle of GLP-1 delivery technologies", Advanced Drug Delivery Reviews, (2018) 130: 113-130.
Zhang et al., "Semaglutide is Neuroprotective and Reduces α-Synuclein Levels in the Chronic MPTP Mouse Model of Parkinson's Disease", J Parkinsons Dis (2019) 9(1): 157-171.
FDA.gov: "FDA Approves New Drug Treatment for Chronic Weight Management, First Since 2014", Jun. 4, 2021, retrieved from: URL:< https://www.fda.gov/news-events/press-announcements/fda-approves-new-drug-treatment-chronic-weight-management-first-2014> [retrieved on Jan. 20, 2022] 3 pages.
Huthmacher et al., (2020) Efficacy and Safety of Short- and Long-Acting Glucagon-Like Peptide 1 Receptor Agonists on a Background of Basal Insulin in Type 2 Diabetes: a Meta-analysis. Diabetes Care 43(9): 2303-2312.
Wu et al., (2016) Liraglutide-loaded poly(lactic-co-glycolic acid) microspheres: Preparation and in vivo evaluation. Eur J Pharm Sci 92: 28-38.
Giri et al., (2013) Prospects of pharmaceuticals and biopharmaceuticals loaded microparticles prepared by double emulsion technique for controlled delivery. Saudi Pharm J 21(2): 125-141.
Zhang et al., (2009) Inhibition of peptide acylation in PLGA microspheres with water-soluble divalent cationic salts. Pharm Res 26(8): 1986-1994.

\* cited by examiner

*Primary Examiner* — Kevin S Orwig
(74) *Attorney, Agent, or Firm* — ROTHWELL, FIGG, ERNST & MANBECK, P.C.

(57) ABSTRACT

The present invention provides parenteral pharmaceutical compositions comprising therapeutically effective amounts of semaglutide or pharmaceutically acceptable salts thereof, the parenteral pharmaceutical compositions are formulated in depot form and provide low-burst release and a continued release profile. The present invention further provides methods of use of the parenteral pharmaceutical compositions for treating type-2 diabetes mellitus, obesity, and Parkinson's disease.

19 Claims, 10 Drawing Sheets

SEMAGLUTIDE DEPOT SYSTEMS AND USE THEREOF

CROSS REFERENCE TO RELATED APPLICATION(S)

This application claims priority to U.S. Provisional Application No. 63/218,405, filed Jul. 5, 2021. The entirety of the disclosure of the above-referenced application is incorporated herein by reference.

FIELD OF THE INVENTION

The present invention relates to parenteral sustained release pharmaceutical compositions comprising semaglutide and use thereof in the treatment of type-2 diabetes mellitus, obesity and Parkinson's Disease.

BACKGROUND OF THE INVENTION

Diabetes mellitus type II or type-2 diabetes (formerly called non-insulin-dependent diabetes mellitus (NIDDM), or adult-onset diabetes) is a disorder that is characterized by high blood glucose levels associated with insulin resistance and relative insulin deficiency. While it is often initially managed by increasing exercise and dietary modifications, medications are typically needed as the disease progresses.

Despite advances in the treatment of type-2 diabetes, optimal glycemic control is often not achieved. Hypoglycemia and weight gain associated with many antidiabetic medications may interfere with the implementation and long-term application of intensive therapies. Current treatments have centered on increasing insulin availability (either through direct insulin administration or through agents that promote insulin secretion), improving sensitivity to insulin, delaying the delivery and absorption of carbohydrates from the gastrointestinal tract, or increasing urinary glucose excretion.

Glucagon-like peptide-1 (GLP-1) is a natural peptide of 30 amino acid residues which is secreted by intestinal cells after meals. It stimulates glucose-dependent insulin release and suppresses postprandial glucagon secretion. GLP-1 is not highly efficacious when administered as a therapeutic agent due to its short pharmacokinetic half-life, i.e., approximately 2-5 min., mainly because it is sensitive to enzymatic degradation by the dipeptidyl-peptidase enzyme (DPP-4). In order to lengthen the half-life of GLP-1, metabolically stable GLP-1 analogs containing chemical modifications and amino acid substitutions, have been developed.

Semaglutide was designed to have an extended circulating human half-life by increased albumin binding with the aim of providing a release profile suitable for once weekly administration. The sequence of liraglutide (a modified acylated version of the human GLP-1 peptide) was derivatized at position 8 with a 2-aminoisobutyric acid (Aib) group, and the arginine at position 34 and glycine at position 37 were maintained. The fatty acid moiety and the linking chemistry to the Lys at position 26 were the key features to providing the desired increase in albumin binding affinity; replacement of Lys26(γGlu-C16 acid) in liraglutide with the extended Lys26(γGlu-2xOEG-C18 acid) provided semaglutide ([Aib8, Lys26(γGlu-2xOEG-C18 acid), Arg34]-hGLP-1-(7-37)-OH), which has a binding affinity of 0.38 nM and a functional potency of 6.2 pM at the human GLP-1 receptor. Incorporation of the Aib amino acid residue at position 8 stabilized semaglutide via protection from DPP-4 enzyme degradation, and when combined with the increased albumin affinity, the plasma half-life was extended to 46.1 hours following IV administration and a mean residence time of 63.6 hours after SC dosing in mini-pigs. In a db/db mouse model (a hyperglycemic, hyperinsulinemic obese model of type-2 diabetes), semaglutide produced sustained dose-dependent efficacy with an $ED_{50}$<2 nmol/kg (Suzuki et al., J. Med. Chem., 2020, 13; 63(3): 905-927; doi: 10.1021/acs.jmedchem.9b00835).

Semaglutide is indicated as an adjunct to diet and exercise to improve glycemic control in adults with type 2 diabetes mellitus and to reduce the risk of major adverse cardiovascular events in adults with type 2 diabetes mellitus and established cardiovascular disease. Recently the U.S. Food and Drug Administration (FDA) has approved the use of semaglutide once-weekly injection for chronic weight management in adults with obesity or overweight status and at least one weight-related condition (e.g. high blood pressure, type 2 diabetes, and high cholesterol).

WO 2020/210764 describes a depot comprising a therapeutic region comprising a therapeutic agent, and a control region comprising a bioresorbable polymer and a releasing agent mixed with the polymer. The releasing agent may be configured to dissolve when the depot is placed in vivo to form diffusion openings in the control region. The depot may be configured to be implanted at a treatment site in vivo and, while implanted, release the therapeutic agent at the treatment site for an extended period of time.

WO 2018/136909 describes a method for producing microparticles of an active ingredient via an in-line recirculating mixing system, wherein the in-line recirculating mixing system comprises a mixer and a conduit coupled to the mixer.

U.S. 2020/0298196 describes a method for producing biodegradable microspheres having improved safety and storage stability, and a method for producing the same.

WO 2020/028907 describes compositions including GLP-1 or an analogue thereof such as exenatide, liraglutide, lixisenatide, albiglutide, dulaglutide, semaglutide, or taspoglutide, entrapped in or incorporated into polymeric particles.

WO 2021/020885 describes a pharmaceutical composition for treatment or prevention of levodopa-induced dyskinesia. When administered in combination with levodopa, the GLP-1 receptor agonist or a controlled release formulation thereof exhibits the effects of decreasing serious side effects caused by long-term administration of levodopa and reducing levodopa-induced, non-spontaneous dyskinesia.

CN 110101846 describes low-sudden-release-rate semaglutide microspheres and a preparation method thereof. The preparation is a long-acting injection prepared from the active ingredient semaglutide with the weight being 1-20% of the weight of the microspheres, a biocompatible polymer substrate with the weight being 60-99% of the weight of the microspheres, and other pharmaceutically acceptable auxiliary materials with the weight being 0-20% of the weight of the microspheres.

U.S. 2019/0133952 describes a preparation method of sustained-release microparticles, characterized by comprising the following steps: 1) preparing a solid dispersion of a water-soluble drug and a biodegradable and biocompatible poorly water-soluble polymer; 2) dissolving the solid dispersion prepared in step 1) in an organic solvent C to form a solid dispersion emulsion, the organic solvent C being an organic solvent which is not capable of dissolving the water-soluble drug but capable of dissolving the poorly water-soluble polymer, has a boiling point lower than that of water and is insoluble or poorly soluble in water; 3) adding the solid dispersion emulsion obtained in step 2) into a surfactant-containing aqueous solution to form a uniform emulsion; and 4) solidifying microparticles in the emulsion by solvent volatilization or solvent extraction, collecting the microparticles, washing with ultrapure water several times to remove the surfactant attached to the surface of the microparticles, and drying to obtain the sustained-release microparticles.

There remains an unmet need for improved long-acting formulations of semaglutide that can provide safe and effective release of the active ingredient over an extended period of time.

SUMMARY OF THE INVENTION

The present invention provides parenteral pharmaceutical compositions comprising therapeutically effective amounts of GLP-1 receptor agonists, in particular semaglutide, or pharmaceutically acceptable salts thereof, wherein the parenteral pharmaceutical compositions are formulated in a depot form. The present invention further provides methods of treating type-2 diabetes mellitus, obesity and Parkinson's Disease comprising administering to a subject in need thereof the parenteral pharmaceutical compositions of the present invention.

The present invention is based, in part, on the surprising discovery that a depot formulation of semaglutide and a biodegradable carrier comprising, e.g., polylactides, polyglycolides and/or polycaprolactones, provides long-acting therapeutically effective plasma concentrations of the semaglutide active ingredient for at least 6 weeks following a single administration. The formulation of the present invention is effective in reducing HbA1c and plasma glucose levels and provides equal or superior therapeutic efficacy to the once weekly injectable dosage forms of semaglutide with reduced incidence of side effects and/or with reduced severity of side effects. By comparison to formulations derived from other sustained release drug delivery technologies, the semaglutide sustained release formulation of the present invention provides a superior release kinetics with minimal burst, increased duration of drug release with less frequent injections, continued constant plasma levels, and improved local tissue tolerance due to a small injection volume.

Thus, in one aspect, the present invention provides a long-acting parenteral pharmaceutical composition comprising microparticles comprising dried water-in-oil-in-water (w/o/w) double emulsion droplets comprising an internal aqueous phase comprising a therapeutically effective amount of semaglutide or a pharmaceutically acceptable salt thereof; a water immiscible polymeric phase comprising a biodegradable carrier selected from the group consisting of polylactides, polyglycolides, polycaprolactones, and combinations thereof; and an external aqueous phase, wherein the composition is in depot form suitable for administration at a medically acceptable location in a subject in need thereof at a frequency of once every four weeks to once every six months, including each value within the specified range.

In one embodiment, the composition provides a twenty-four hour semaglutide burst release of less than 20% of the administered dose following administration. In another embodiment, the composition provides an in vitro semaglutide release in 1 day in a phosphate buffer at pH 7.4 of less than 20%. In yet another embodiment, the composition provides an in vitro semaglutide release in 14 days in a phosphate buffer at pH 7.4 of less than 80%. In yet another embodiment, the composition provides an in vitro semaglutide release in 28 days in a phosphate buffer at pH 7.4 of more than 80%.

In another embodiment, semaglutide is released from the composition in a continuous manner.

In yet another embodiment, semaglutide is released from the composition in a controlled release order selected from zero, first, second and third release order, and any pseudo orders thereof. Each possibility represents a separate embodiment.

In particular embodiments, semaglutide is present in the pharmaceutical composition as the sole active ingredient.

In various embodiments, the biodegradable carrier is a biodegradable polymer selected from the group consisting of poly (D,L-lactide-co-glycolide) (PLGA), poly (D,L-lactide) (PLA), polyglycolide (PGA), polycaprolactone (PCL), and combinations thereof. Each possibility represents a separate embodiment. In one currently preferred embodiment, the biodegradable carrier is poly (D,L-lactide-co-glycolide) (PLGA). In another currently preferred embodiment, the biodegradable carrier is poly (D,L-lactide) (PLA). In yet another currently preferred embodiment, the biodegradable carrier is poly (D,L-lactide)-polycaprolactone (PLA-PCL). In an additional currently preferred embodiment, the biodegradable carrier is a mixture of poly (D,L-lactide-co-glycolide) and poly (D,L-lactide)-polycaprolactone (PLGA/PLA-PCL).

In some embodiments, each of the internal and external aqueous phases, independently, further comprise a surfactant. In particular embodiments, the surfactant is selected from the group consisting of polyvinyl alcohol (PVA), polysorbate, polyethylene oxide-polypropylene oxide block copolymers, polyethylene glycol, and cellulose esters. Each possibility represents a separate embodiment. In a currently preferred embodiment, the surfactant is PVA. In another currently preferred embodiment, the surfactant is polyethylene glycol.

In other embodiments, each of the internal and external aqueous phases, independently, further comprise a tonicity modifier. In certain embodiments, the tonicity modifier is an ionic tonicity modifier comprising sodium chloride. In further embodiments, the tonicity modifier is a non-ionic tonicity modifier comprising a sugar or a sugar alcohol. In specific embodiments, the sugar is sucrose.

In additional embodiments, the water immiscible polymeric phase further comprises a surfactant comprising a fatty acid or a derivative thereof. In particular embodiments, the surfactant is lecithin, hydroxylated lecithin, stearic acid, or a mixture or combination thereof. Each possibility represents a separate embodiment.

In some embodiments, the ratio of semaglutide or a pharmaceutically acceptable salt thereof to the biodegradable carrier is in the range of about 1:2 to about 1:30 (w/w) including all iterations of ratios within the specified range.

In certain embodiments, the depot composition of the present invention is prepared by a water-in-oil-in-water (w/o/w) double emulsification process comprising the steps of:
(i) dispersing an aqueous suspension or solution of semaglutide or a pharmaceutically acceptable salt thereof in a solution of the biodegradable carrier in a water-immiscible volatile organic solvent, thereby obtaining a water-in-oil emulsion; and
(ii) dispersing said water-in-oil emulsion in a continuous external water phase comprising a surfactant, to form a water-in-oil-in-water (w/o/w) double emulsion droplets.

In several embodiments, the process further comprises the step of (iii) collecting the thus formed microparticles by filtration or centrifugation. In other embodiments, the process further comprises the step of (iv) washing the collected microparticles. In one embodiment, washing is performed with purified water, a buffered solution, the external aqueous phase, or a mixture or combination thereof. Each possibility represents a separate embodiment. In another embodiment, washing is performed with an aqueous solution comprising divalent cations. In further embodiments, the process further comprises the step of drying the collected or washed microparticles. In one embodiments, drying the collected or washed microparticles is performed by lyophilization. In additional embodiments, the process further comprises the step of reconstituting the dried microparticles in a physiologically acceptable solvent prior to administration.

In some embodiments, the internal aqueous phase has a pH of about 7 to about 9, including each value within the specified range. In other embodiments, the internal aqueous phase has a pH of about 7.5 to about 9.5, including each value within the specified range. In yet other embodiments, the internal aqueous phase has a pH of about 7.8. In various embodiments, the pH is adjusted by an acid or a base. Each possibility represents a separate embodiment. Preferably, the pH is adjusted using sodium hydroxide.

In additional embodiments, the depot composition of the present invention is in the form of solid microparticles, a solution or a suspension. Each possibility represents a separate embodiment of the present invention. In currently preferred embodiments, the composition is in the form of a suspension comprising solid microparticles suspended in a physiologically acceptable solvent.

In further embodiments, the composition is suitable for a dosing schedule from about once every four weeks to about once every six months, including each value within the specified range. In other embodiments, the composition releases the semaglutide active ingredient over a period of about one month to about three months, including each value within the specified range. In additional embodiments, the composition releases the semaglutide active ingredient over a period of about four weeks to about six weeks, including each value within the specified range. In a currently preferred embodiment, the composition releases the semaglutide active ingredient over a period of about one month to about two months, including each value within the specified range.

In other embodiments, the composition is administered at a semaglutide dose of about 5 mg to about 100 mg, including each value within the specified range. In some embodiments, the composition is administered intramuscularly.

As contemplated herein, the compositions of the invention are useful in treating subjects afflicted with diabetes, in particular type-2 diabetes mellitus.

Thus, in some embodiments, the present invention provides a method of treating type-2 diabetes mellitus, the method comprising the step of administering to a subject in need thereof a parenteral pharmaceutical composition as disclosed herein at a frequency of once every four weeks to once every six months, including each value within the specified range. In one embodiment, said treatment comprises reducing fasting glucose levels in said subject by at least about 5%, preferably by at least about 10%, more preferably by at least about 15%, most preferably by at least about 20%. Each possibility represents a separate embodiment. In another embodiment, said treatment comprises reducing fed glucose levels in said subject by at least about 5%, preferably by at least about 10%, more preferably by at least about 15%, most preferably by at least about 20%. Each possibility represents a separate embodiment. In yet another embodiment, said treatment comprises reducing hemoglobin A1c (HbA1c) levels in said subject by at least about 5%, preferably by at least about 10%, more preferably by at least about 15%, most preferably by at least about 20%. Each possibility represents a separate embodiment.

According to additional embodiments, the compositions of the invention are useful in treating subjects afflicted with Parkinson's Disease. Thus, in some embodiments, the present invention provides a method of treating Parkinson's Disease, comprising the step of administering to a subject in need thereof a parenteral pharmaceutical composition as disclosed herein at a frequency of once every four weeks to once every six months, including each value within the specified range.

According to further embodiments, the compositions of the invention are useful in treating obesity. Thus, in some embodiments, the present invention provides a method of treating obesity, the method comprising the step of administering to a subject in need thereof a parenteral pharmaceutical composition as disclosed herein at a frequency of once every four weeks to once every six months, including each value within the specified range.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 1A: MPS-23; FIG. 1B: MPS-25; FIG. 1C: MPS-27M; FIG. 1D: MPS-34HL; FIG. 1E: MPS-40; FIG. 1F: MPS-41; FIG. 1G: MPS-43; FIG. 1H: MPS-44; FIG. 1I MPS-08; FIG. 1J: MPS-15; FIG. 1K: MPS-45; FIG. 1L: MPS-46.

FIG. 4A shows the in vitro release of semaglutide from depot formulation MPS-46; FIG. 4B shows the % semaglutide content in the MPS-46 depot formulation during the dissolution testing.

FIG. 9A: Groups 1—Naïve control (●) and Group 2—Vehicle control (■); FIG. 9B: Group 2—Vehicle control (■) and Group 3—semaglutide 0.06 mg/kg SC daily (1); FIG. 9C: Group 2—Vehicle control (■) and Group 4—semaglutide 0.4 mg/kg SC daily (▼); FIG. 9D: Group 2—Vehicle control (■) and Group 5—semaglutide depot (◆). Data is shown as mean+SEM.

FIG. 10A: Group 3—semaglutide 0.06 mg/kg SC daily; FIG. 10B: Group 4—semaglutide 0.4 mg/kg SC daily; FIG. 10C: Group 5—semaglutide depot. Data is shown as mean+SEM. FIG. 10D: semaglutide depot following a single IM administration (▲) vs. semaglutide solution administered subcutaneously every 24 h (●).

DETAILED DESCRIPTION OF THE INVENTION

Figure 1A:
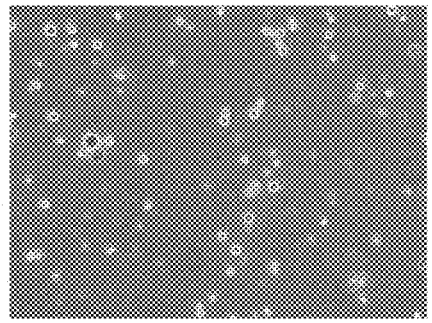
FIGS. 1A-1L: show microscopic images of exemplary microparticles prepared according to the formulations detailed in Example 1.
Figure 1B:
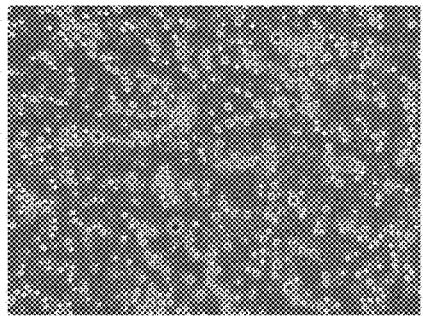
Figure 1C:
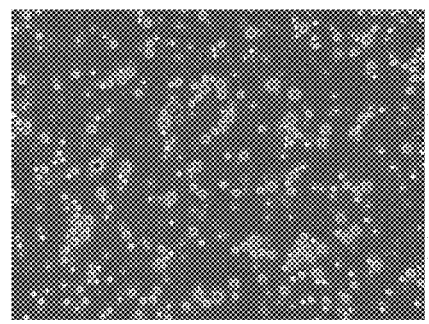
Figure 1D:
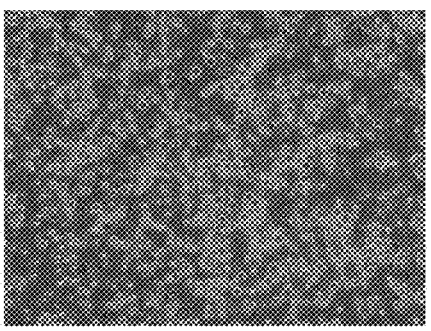
Figure 1E:
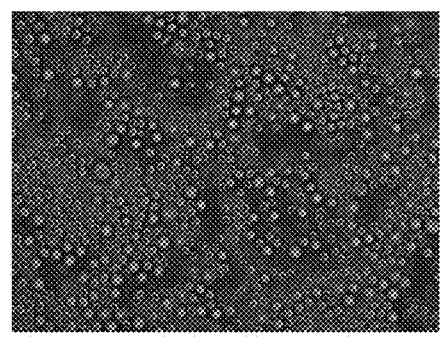
Figure 1F:
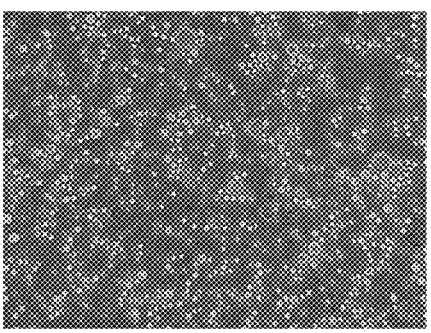
Figure 1G:
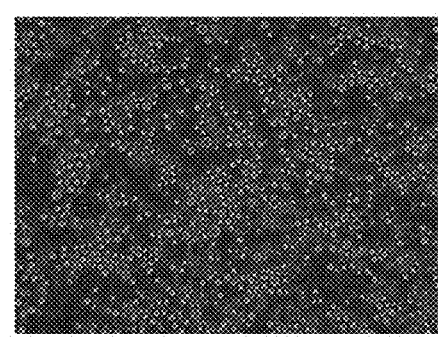
Figure 1H:
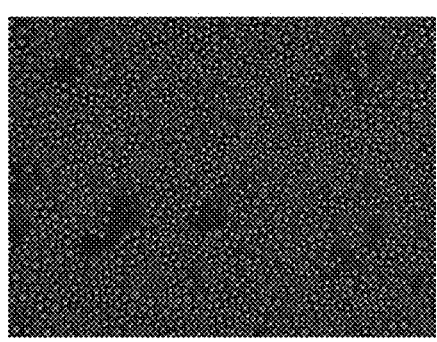
Figure 1I:
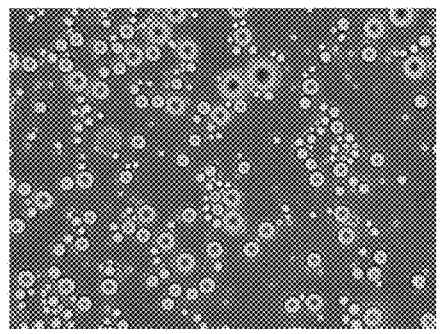
Figure 1J:
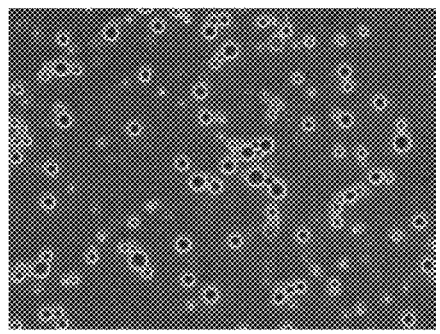
Figure 1K:
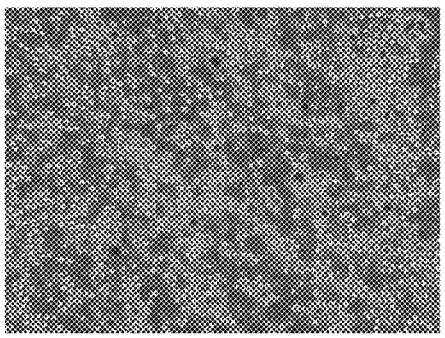
Figure 1L:
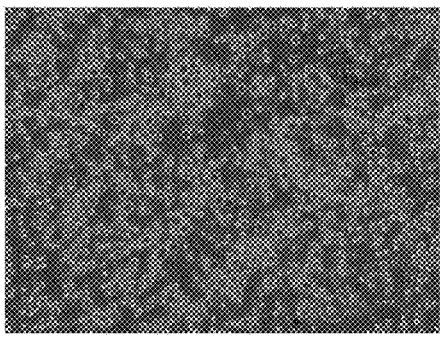

The present invention provides long-acting pharmaceutical preparations of semaglutide or pharmaceutically acceptable salts thereof which afford equal or superior therapeutic efficacy to the once weekly compositions but are designed for administration at a frequency of once every four weeks to once every six months and thus result in improved patient compliance. In addition to providing the same or superior therapeutic efficacy, the pharmaceutical preparations of the invention reduce side effects (local and/or systemic), resulting from frequent injections of semaglutide including lipoatrophy, lipohypertrophy, local allergic reactions, abscess formation and scarring. The present invention further provides low-burst release semaglutide depot formulations that provide continuous release of the active ingredient thereby avoiding the undesired release of high concentrations of semaglutide shortly after administration or the lag in semaglutide release following administration thus resulting in improved glycemic control and prevention of events of hypoglycemia and hyperglycemia within the first 48 hours following administration.

According to some aspects and embodiments, the pharmaceutical formulations and dosages of the invention are conveniently provided in a form suitable for parenteral administration, for example by injection, implantation or infusion. Each possibility represents a separate embodiment of the invention. The term "parenteral" as used herein refers to routs of administration selected from subcutaneous (SC), intravenous (IV), intramuscular (IM), intradermal (ID), intraperitoneal (IP), and the like. Each possibility represents a separate embodiment of the invention. In currently preferred embodiments, the pharmaceutical composition is administered via the intramuscular (IM) route.

Within the scope of the present invention are sustained release depot formulations. The term "sustained" as used herein refers to a pharmaceutical composition which provides prolonged, long or extended release of a therapeutically effective amount of semaglutide or any pharmaceutically acceptable salt thereof, to the general systemic circulation of a subject or to local sites of action in a subject. This term may further refer to a pharmaceutical composition which provides prolonged, long or extended exposure to (pharmacokinetics) and duration of action of (pharmacodynamics) a therapeutically effective amount of semaglutide or any pharmaceutically acceptable salt thereof, in a subject. In particular, the sustained release pharmaceutical composition of the present invention provides a dosing regimen of once every four weeks, once a month, once every month and a half, once every two months, once every three months, once every four months, once every five months, or once every six months. Each possibility represents a separate embodiment of the invention.

Depending on the duration of action required, each depot or implantable device of the present invention, is designed to afford the release of semaglutide or a pharmaceutically acceptable salt thereof over a period selected from the group consisting of four weeks, a month, a month and a half, two months, two months and a half, three months, three months and a half, four months, four months and a half, five months, five months and a half, and six months. Each possibility represents a separate embodiment.

The depot system of the present invention encompasses any form known to a person of skill in the art. According to some embodiments, the depot system is present in a form selected from the group consisting of biodegradable microspheres, non-biodegradable microspheres, implants of any suitable geometric shape, prolonged release gels, and erodible matrices. Each possibility represents a separate embodiment. According to certain embodiments, the implant of any suitable geometric shape is selected from the group consisting of implantable capsules, implantable rods and implantable rings. Each possibility represents a separate embodiment of the invention.

According to some embodiments, a suitable form of parenteral pharmaceutical compositions includes, but is not limited to, an injectable composition containing microparticles. The microparticles comprise a therapeutically effective amount of the active ingredient which is entrapped in a biodegradable or non-biodegradable polymer. Each possibility represents a separate embodiment of the invention. In certain embodiments, the microparticles comprise semaglutide in an amount ranging from about 30 mg to about 130 mg per 1 gram of microparticles, including each value within the specified range. In other embodiments, the microparticles comprise semaglutide in an amount ranging from about 50 mg to about 100 mg per 1 gram of microparticles, including each value within the specified range. In various embodiments, the microparticles comprise dried water-in-oil-in-water (w/o/w) double emulsion droplets. The double emulsion droplets, according to the principles of the present invention, comprise an internal aqueous phase comprising a therapeutically effective amount of semaglutide or a pharmaceutically acceptable salt thereof; a water immiscible polymeric phase comprising a biodegradable carrier selected from the group consisting of polylactides, polyglycolides, polycaprolactones, and combinations thereof; and an external aqueous phase.

According to the principles of the present invention, semaglutide may be present in the composition in the form of free base or in the form of its salts or mixtures thereof. Each possibility represents a separate embodiment. Representative examples of salts include, but are not limited to, salts with suitable inorganic acids such as hydrochloric acid, hydrobromic acid, and the like. Each possibility represents a separate embodiment. Representative examples of salts also include, but are not limited to, salts with organic acids such as formic acid, acetic acid, propionic acid, lactic acid, tartaric acid, ascorbic acid, citric acid, and the like. Each possibility represents a separate embodiment. Representative examples of salts also include, but are not limited to, salts with bases such as triethanolamine, diethylamine, meglumine, arginine, alanine, leucine, diethylethanolamine, olamine, triethylamine, tromethamine, choline, trimethylamine, taurine, benzamine, methylamine, dimethylamine, trimethylamine, methylethanolamine, propylamine, isopropylamine, adenine, guanine, cytosine, thymine, uracil, thymine, xanthine, hypoxanthine, and the like. Each possibility represents a separate embodiment. According to further embodiments, pharmaceutically acceptable salts include acid addition salts such as those containing sulfate, phosphate, sulfamate, methanesulfonate, ethanesulfonate, benzenesulfonate, p-toluenesulfonate, cyclohexylsulfamate, and quinate. Each possibility represents a separate embodiment.

Salts according to the principles of the present invention may be prepared by, for example, reacting the free acid or free base forms with one or more equivalents of the appropriate base or acid, respectively, in a solvent or medium in which the salt is insoluble, or in a solvent such as water which is then removed in vacuo, by freeze-drying, or by exchanging the ions of an existing salt for another ion on a suitable ion exchange resin. Each possibility represents a separate embodiment of the invention.

According to various aspects and embodiments, semaglutide or a salt thereof is present in the parenteral compositions disclosed herein as the sole active ingredient. Typically semaglutide or semaglutide salt is present in the parenteral compositions of the invention in a therapeutically effective amount. As used herein, the term "therapeutically effective amount" is intended to qualify the amount of semaglutide or semaglutide salt, that provides the following responses after administration of the parenteral composition: stimulation of glucose-dependent insulin release and/or suppression of postprandial glucagon secretion in patients with type-2 diabetes. In some embodiments, semaglutide or semaglutide salt is present in the parenteral compositions disclosed herein at a dose of about 5 mg to about 100 mg, including each value within the specified range. Typical doses within the scope of the present invention include, but are not limited to, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg. Each possibility represents a separate embodiment.

The internal aqueous phase, according to the principles of the present invention may further comprising a surfactant and/or a tonicity modifier. Suitable surfactants include, but are not limited to, polyvinyl alcohol (PVA), polysorbate, polyethylene oxide-polypropylene oxide block copolymers, polyethylene glycol, and cellulose esters. Each possibility represents a separate embodiment. Currently preferred embodiments include the use of PVA and/or PEG. Suitable tonicity modifiers include, but are not limited to, ionic tonicity modifiers and non-ionic tonicity modifiers such as, sodium chloride, a sugar (e.g. sucrose) or a sugar alcohol (e.g. mannitol, sorbitol). Each possibility represents a separate embodiment.

In certain embodiments, the dosage forms include, but are not limited to, biodegradable injectable depot systems such as, PLGA based injectable depot systems, non-PLGA based injectable depot systems, and injectable biodegradable gels or dispersions. Each possibility represents a separate embodiment of the invention. The term "biodegradable" as used herein refers to a component which erodes or degrades at its surfaces over time due, at least in part, to contact with substances found in the surrounding tissue fluids, or by cellular action. Suitable biodegradable or non-biodegradable depot systems within the scope of the present invention include, but are not limited to, systems comprising at least one of the following polymers: polyanhydrides; poly(sebacic acid) SA; poly(ricinoleic acid) RA; poly(fumaric acid), FA; poly(fatty acid dimmer), FAD; poly(terephthalic acid), TA; poly(isophthalic acid), IPA; poly(p-{carboxyphenoxy}methane), CPM; poly(p-{carboxyphenoxy} propane), CPP; poly(p-{carboxyphenoxy}hexane) CPH; polyamines, polyurethanes, polyesteramides, polyorthoesters {CHDM: cis/trans-cyclohexyl dimethanol, HD:1,6-hexanediol, DETOU: (3 ,9-diethylidene-2, 4, 8,10-tetraoxaspiro undecane)}; polydioxanones; polyhydroxybutyrates; polyalkylene oxalates; polyamides; polyesteramides; polyacetals; polyketals; polycarbonates; polyorthocarbonates; polysiloxanes; polyphosphazenes; succinates; hyaluronic acid; poly(malic acid); poly(amino acids); polyhydroxyvalerates; polyalkylene succinates; polyvinylpyrrolidone; polystyrene; synthetic cellulose esters; polyacrylic acids; polybutyric acid; triblock copolymers (PLGA-PEG-PLGA), triblock copolymers (PEG-PLGA-PEG), poly (N-isopropylacrylamide) (PNIPAAm), poly (ethylene oxide)-poly (propylene oxide)-poly (ethylene oxide) tri-block copolymers (PEO-PPO-PEO), poly valeric acid; polyethylene glycol; polyhydroxyalkylcellulose; chitin; chitosan; polyorthoesters and copolymers, terpolymers; lipids such as cholesterol, lecithin; poly(glutamic acid-co-ethyl glutamate) and the like, or mixtures thereof. Each possibility represents a separate embodiment of the invention.

Additional depot systems within the scope of the present invention include, but are not limited to, systems comprising at least one of the following polymers: poly (D,L-lactide-co-glycolide) (PLGA), poly (D,L-lactide) (PLA), polyglycolide (PGA), polycaprolactone (PCL), polyhydroxybutyrate, polyorthoesters, polyalkaneanhydrides, gelatin, collagen, oxidized cellulose, polyphosphazene, and any combination thereof. Each possibility represents a separate embodiment of the invention.

In particular, the biodegradable polymer comprises, but is not limited to, lactic acid-based polymers such as polylactides e.g. poly (D,L-lactide) i.e. PLA; glycolic acid-based polymers such as polyglycolide (PGA) e.g. Lactel® from Durect; poly (D,L-lactide-co-glycolide) i.e. PLGA, (Resomer® RG-504, Resomer® RG-502, Resomer® RG-504H, Resomer® RG-502H, Resomer® RG-504S, Resomer® RG-502S, from Boehringer, Lactel® from Durect); and polycaprolactones such as poly(ε-caprolactone) i.e. PCL (Lactel® from Durect). Each possibility represents a separate embodiment.

A currently preferred biodegradable polymer is a lactic acid-based polymer, more preferably polylactide, or poly (D, L-lactide-co-glycolide) i.e. PLGA. Another currently preferred biodegradable polymer is polycaprolactone (PCL). Yet another currently preferred biodegradable polymer is polylactic acid (PLA). Further currently preferred biodegradable polymer is PLA-PCL. An additional currently preferred biodegradable polymer is a mixture of PLGA with PLA-PCL. In one embodiment, the weight % ratio of PLGA to PLA-PCL is in the range of 9:1 to 1:9, including all iterations of ratios within the specified range. In another embodiment, the weight % ratio of PLGA to PLA-PCL is in the range of 9:1 to 7:3, including all iterations of ratios within the specified range. In yet another embodiment, the weight% ratio of PLGA to PLA-PCL is 8:2. Typically, the biodegradable polymer is present in an amount of between about 10% and about 98% w/w of the solid composition (e.g. microparticles), including each value within the specified range. However, it is understood that the amount of biodegradable polymer is determined by parameters such as the duration of use and the like. In some embodiments, the lactic acid-based polymer has a monomer ratio of lactic acid to glycolic acid in the range of 100:0 to about 0:100, preferably 100:0 to about 10:90, including each value within the specified ranges. In one embodiment, the lactic acid-based polymer has a monomer ratio of lactic acid to glycolic acid of 80:20. In another embodiment, the lactic acid-based polymer has a monomer ratio of lactic acid to glycolic acid of 75:25. In yet another embodiment, the lactic acid-based polymer has a monomer ratio of lactic acid to glycolic acid of 50:50. In further embodiments, the biodegradable polymer has an average molecular weight of from about 1,000 to about 200,000 Daltons, including each value within the specified range.

According to certain aspects and embodiments, the polymeric phase further comprises a surfactant which may be a fatty acid or a derivative thereof. Suitable surfactants that can be incorporated in the oily phase include, but are not limited to, lecithin, hydroxylated lecithin, stearic acid, or a mixture or combination thereof. Each possibility represents a separate embodiment.

According to the principles of the present invention, the ratio of semaglutide or a pharmaceutically acceptable salt thereof to the biodegradable carrier is typically in the range of about 1:2 to about 1:30 (w/w) including all iterations of ratios within the specified range. Exemplary ratios include, but are not limited to, about 1:2 to about 1:25, about 1:2 to about 1:20, about 1:2 to about 1:15, about 1:2 to about 1:10, about 1:2 to about 1:5, about 1:5 to about 1:30, about 1:5 to about 1:25, about 1:5 to about 1:20, about 1:5 to about 1:15, about 1:5 to about 1:10, about 1:10 to about 1:30, about 1:10 to about 1:25, about 1:10 to about 1:20, about 1:10 to about 1:15, about 1:15 to about 1:30, about 1:15 to about 1:25, about 1:15 to about 1:20, about 1:20 to about 1:30, or about 1:25 to about 1:30 (w/w). Each possibility represents a separate embodiment.

Without being bound by a particular theory it is believed that the release of semaglutide from the depot formulation can occur by either one of two different mechanisms. The first mechanism includes the release by diffusion through aqueous filled channels generated in the polymer matrix, such as by the dissolution of the biologically active agent, or by voids created by the removal of the polymer solvent during the preparation of the sustained release composition. Additional channels may be formed using a pore-former e.g. zinc oxide. The second mechanism includes the release of the biologically active agent due to degradation of the polymer. The rate of degradation can be controlled by tailoring polymer properties that influence its rate of hydration. These properties include, for instance, the ratio of lactide to glycolide comprising a polymer, the use of the L-isomer of a monomer instead of a racemic mixture, and the molecular weight of the polymer. These properties can affect hydrophilicity and crystallinity, which control the rate of hydration of the polymer. By altering the properties of the polymer, the release profile can be controlled. For example, increasing the glycolide content of a poly(lactide-co-glycolide) polymer and decreasing the molecular weight of the polymer can enhance the hydrolysis of the polymer and thus, provide an increased biologically active agent release from polymer erosion.

According to various aspects and embodiments, the release of semaglutide from the composition occurs in a continuous manner The release profile can be a zero order release profile, a first order release profile, a second order release profile, a third order release profile, or any pseudo orders known. Each possibility represents a separate embodiment. According to particular aspects and embodiments, the composition provides a low-burst release providing a twenty-four hour semaglutide release of less than 20% of the administered dose following administration. The release of semaglutide from the formulation can also be determined in vitro. In some embodiments, less than 20% of semaglutide is released from the depot formulation within 1 day in a phosphate buffer at pH 7.4. In other embodiments, less than 80% of semaglutide is released from the depot formulation within 14 days in a phosphate buffer at pH 7.4. In further embodiments, more than 80% of semaglutide is released from the depot formulation within 28 days in a phosphate buffer at pH 7.4.

According to further aspects and embodiments, the emulsion droplets comprise an external aqueous phase. In currently preferred embodiments, the external aqueous phase further comprises at least one of a surfactant and a tonicity modifier as detailed above for the internal aqueous phase.

According to the principles of the present invention, the water-in-oil-in water (w/o/w) double emulsion droplets are subsequently dried to provide dried microparticles. The dried microparticles can be administered as is. According to some aspects and embodiments, the dried microparticles are suspended in an inert oil, suitably a vegetable oil such as sesame, peanut, olive oil, or other acceptable carrier. Each possibility represents a separate embodiment. Preferably, the dried microparticles are suspended in an aqueous carrier, for example, an isotonic buffer solution at a pH of about 3.0 to about 7.0, more preferably of about 4.0 to about 6.0, and most preferably of about 4.0 to about 5.0, including each value within the specified ranges. These compositions may be sterilized by conventional sterilization techniques, or may be sterile filtered. The compositions may contain pharmaceutically acceptable auxiliary substances as required to approximate physiological conditions, such as pH buffering agents. Suitable buffers include, but are not limited to, sodium acetate/acetic acid buffers. The desired isotonicity may be accomplished using sodium chloride or other pharmaceutically acceptable agents such as dextrose, boric acid, sodium tartrate, propylene glycol, polyols (such as mannitol and sorbitol), or other inorganic or organic solutes. Each possibility represents a separate embodiment of the invention. Sodium chloride is preferred particularly for buffers containing sodium ions.

According to some embodiments, carriers or excipients can also be used to facilitate administration of the dosages of the present invention. Examples of carriers and excipients include, but are not limited to, calcium carbonate, calcium phosphate, various sugars such as lactose, or various types of starch, cellulose derivatives, gelatin, vegetable oils, polyethylene glycols and physiologically compatible solvents. Each possibility represents a separate embodiment of the invention.

According to various embodiments, solutions of the dosage forms may be thickened with a thickening agent such as, but not limited to, methylcellulose. They may be prepared in emulsified form, either water-in-oil or oil-in-water. Any of a wide variety of pharmaceutically acceptable emulsifying agents may be employed including, for example, acacia powder, a non-ionic surfactant (such as a Tween), or an ionic surfactant (such as alkali polyether alcohol sulfates or sulfonates, e.g., a Triton). Each possibility represents a separate embodiment of the invention.

According to additional embodiments, the pharmaceutically acceptable carrier is a liquid. According to further embodiments, the liquid is selected from the group consisting of an aqueous solvent or a non-aqueous solvent, emulsions and suspensions. Each possibility represents a separate embodiment. According to other embodiments, the liquid is an aqueous solvent selected from the group consisting of saline, dextrose solutions, and glycerol solutions. Each possibility represents a separate embodiment of the invention.

The compositions of the present invention may further comprise one or more pharmaceutically acceptable excipient(s) selected from, but not limited to, co-surfactants/solubilizers, solvents/co-solvents, water immiscible solvents, water, water miscible solvents, oily components, hydrophilic solvents, emulsifiers, preservatives, antioxidants, anti-foaming agents, stabilizers, buffering or pH adjusting agents, osmotic agents, pore forming agents, osmotic adjustment agents, or any other excipient known in the art. Each possibility represents a separate embodiment. Suitable co-surfactants or solubilizers include, but are not limited to, polyethylene glycols, polyoxyethylene- polyoxypropylene block copolymers known as "poloxamer", polyglycerin fatty acid esters such as decaglyceryl monolaurate and decaglyceryl monomyristate, sorbitan fatty acid ester such as sorbitan monostearate, polyoxyethylene sorbitan fatty acid ester such as polyoxyethylene sorbitan monooleate (Tween), polyethylene glycol fatty acid ester such as polyoxyethylene monostearate, polyoxyethylene alkyl ether such as polyoxyethylene lauryl ether, polyoxyethylene castor oil and hardened castor oil such as polyoxyethylene hardened castor oil, and the like or mixtures thereof. Each possibility represents a separate embodiment of the invention. Suitable solvents/co-solvents include, but not limited to, alcohols, triacetin, dimethyl isosorbide, glycofurol, propylene carbonate, water, dimethyl acetamide, and the like or mixtures thereof. Each possibility represents a separate embodiment of the invention. Suitable anti-foaming agents include, but are not limited to, silicon emulsions or sorbitan sesquioleate. Each possibility represents a separate embodiment of the invention. Suitable stabilizers to prevent or reduce the deterioration of the components in the compositions of the present invention include, but are not limited to, antioxidants such as glycine, a-tocopherol or ascorbate, BHA, BHT, and the like or mixtures thereof. Each possibility represents a separate embodiment of the invention. Suitable tonicity modifiers include, but are not limited to, mannitol, sodium chloride, and glucose. Each possibility represents a separate embodiment of the invention. Suitable buffering agents include, but are not limited to, acetates, phosphates, and citrates with suitable cations. Each possibility represents a separate embodiment of the invention.

The sustained release depot systems of the present invention can be prepared by any manner known in the art. Currently preferred is the incorporation of semaglutide or a pharmaceutically acceptable salt thereof into a colloidal delivery system, e.g., biodegradable microparticles, thus allowing release retardation by diffusion through polymeric walls of the particle and by polymer degradation in water media or biological fluids in the body. In some embodiments, the biodegradable microparticles are devoid of any coating layer.

According to some embodiments, the sustained-release microparticles of the present invention are prepared in the form of injectable dried microparticles by a process known as the "double emulsification". Briefly, a concentrated aqueous solution or suspension of semaglutide or a pharmaceutically acceptable salt thereof optionally comprising a surfactant (e.g. polyvinyl alcohol—PVA, polysorbates, polyethylene oxide-polypropylene oxide block copolymers, cellulose esters and the like) and/or a tonicity modifier (e.g. sucralose) is prepared. The pH of the aqueous solution is typically adjusted to a range of about 7 to about 9, or about 7.5 to about 9.5, including each value within the specified range. Adjustment of the pH can be performed using any acid or base, for example sodium hydroxide. The aqueous solution or suspension is then dispersed in a solution of a biodegradable or non-biodegradable polymer in a water-immiscible volatile organic solvent (e.g. methylene chloride, chloroform and the like) optionally comprising a surfactant (e.g. a fatty acid or derivative thereof such as hydrogenated lecithin). The thus obtained "water-in-oil" (w/o) emulsion is then dispersed in a continuous external water phase containing a surfactant (e.g. polyvinyl alcohol—PVA, polysorbates, polyethylene oxide-polypropylene oxide block copolymers, cellulose esters and the like) and optionally a tonicity modifier (e.g. sodium chloride) to form "water-in-oil-in-water (w/o/w) double emulsion" droplets. After evaporation of the organic solvent, the microparticles solidify and are collected by filtration or centrifugation. The terms "oil phase" and "water-immiscible phase" may be used interchangeably herein. The collected microparticles (MPs) are washed (e.g. with purified water, a buffer solution such as a phosphate buffer, the external aqueous solution or a mixture thereof or with an aqueous solution comprising divalent cations, e.g. magnesium, calcium, zinc and the like or a mixture thereof) to eliminate most of the surfactant and free peptide and centrifuged again. The washed MPs are collected and dried (e.g. lyophilized) without additives or with the addition of a cryoprotectant (mannitol) to facilitate their subsequent reconstitution.

According to further embodiments, the particle size of the "water-in-oil-in-water (w/o/w) double emulsion" droplets can be controlled by various parameters including, but not limited to, the amount of applied force, the speed of mixing, surfactant type and concentration, etc. Following solidification, the microparticles are typically characterized by particle sizes in the range of from about 1 to about 100 μm, including each value within the specified range. For example, the microparticles typically have sizes ranging from about 3 to about 50 μm, from about 3 to about 40 μm, or from about 3 to about 30 μm, with each possibility representing a separate embodiment of the present invention.

Methods of Use

The present invention provides a method for treating or delaying the progression or onset of diabetes, especially type-2 diabetes, including complications of diabetes, such as retinopathy, neuropathy, nephropathy and delayed wound healing, and related diseases such as insulin resistance (impaired glucose homeostasis), hyperglycemia, hyperinsulinemia, elevated blood levels of fatty acids or glycerol, obesity, hyperlipidemia including hypertriglyceridemia, Syndrome X, atherosclerosis, hypertension, and cardiovascular diseases and events such as coronary heart disease, cerebrovascular disease, peripheral arterial disease, rheumatic heart disease, congenital heart disease, deep vein thrombosis and pulmonary embolism, non-fatal myocardial infarction, or non-fatal stroke, and for increasing high density lipoprotein levels. The method comprises administering a long-acting parenteral pharmaceutical composition comprising microparticles comprising dried water-in-oil-in-water (w/o/w) double emulsion droplets comprising an internal aqueous phase comprising a therapeutically effective amount of semaglutide or a pharmaceutically acceptable salt thereof; a water immiscible polymeric phase comprising a biodegradable carrier selected from the group consisting of polylactides, polyglycolides, polycaprolactones, and combinations thereof; and an external aqueous phase, wherein the composition is in depot form suitable for administration at a medically acceptable location in a subject in need thereof at a frequency of once every four weeks to once every six months.

The term "treating" as used herein with reference to type-2 diabetes refers to suppression or alleviation of short- and long-term symptoms and complications associated with type-2 diabetes, for example hyperglycemia, and any one of the aforementioned complications. In various embodiments, the compositions disclosed herein reduce fasting glucose levels by at least about 5%, preferably by at least about 10%, more preferably by at least 15%, and most preferably by at least 20%. In other embodiments, the compositions disclosed herein reduce fed glucose levels by at least about 5%, preferably by at least about 10%, more preferably by at least about 15%, and most preferably by at least 20%. In further embodiments, the compositions disclosed herein reduce hemoglobin A1c (HbA1c) levels in said subject by at least about 5%, preferably by at least about 10%, more preferably by at least about 15%, and most preferably by at least 20%. The aforementioned reduction in fasting glucose levels, fed glucose levels, and hemoglobin A1c (HbA1c) levels are contemplated for at least about four weeks to about 6 months or any time period therebetween after a single administration.

Within the scope of the present invention are fasting glucose levels after a single parenteral administration of the composition of the invention of between about 70 and about 400 mg/dL, including each value within the specified range. For example, fasting glucose levels after a single parenteral administration include, but are not limited to, about 70 mg/dL, about 75 mg/dL, about 80 mg/dL, about 85 mg/dL, about 90 mg/dL, about 95 mg/dL, about 100 mg/dL, about 110 mg/dL, about 120 mg/dL, about 130 mg/dL, about 140 mg/dL, about 150 mg/dL, about 160 mg/dL, about 170 mg/dL, about 180 mg/dL, about 190 mg/dL, about 200 mg/dL, about 210 mg/dL, about 220 mg/dL, about 230 mg/dL, about 240 mg/dL, about 250 mg/dL, about 260 mg/dL, about 270 mg/dL, about 280 mg/dL, about 290 mg/dL, about 300 mg/dL, about 310 mg/dL, about 320 mg/dL, about 330 mg/dL, about 340 mg/dL, about 350 mg/dL, about 360 mg/dL, about 370 mg/dL, about 380 mg/dL, about 390 mg/dL, and about 400 mg/dL. Each possibility represents a separate embodiment.

Within the scope of the present invention are fed glucose levels after a single parenteral administration of the composition of the present invention of between about 120 and about 650 mg/dL, including each value within the specified range. For example, fed glucose levels after a single parenteral administration include, but are not limited to about 120 mg/dL, about 130 mg/dL, about 140 mg/dL, about 150 mg/dL, about 160 mg/dL, about 170 mg/dL, about 180 mg/dL, about 190 mg/dL, about 200 mg/dL, about 210 mg/dL, about 220 mg/dL, about 230 mg/dL, about 240 mg/dL, about 250 mg/dL, about 260 mg/dL, about 270 mg/dL, about 280 mg/dL, about 290 mg/dL, about 300 mg/dL, about 310 mg/dL, about 320 mg/dL, about 330 mg/dL, about 340 mg/dL, about 350 mg/dL, about 360 mg/dL, about 370 mg/dL, about 380 mg/dL, about 390 mg/dL, about 400 mg/dL, about 410 mg/dL, about 420 mg/dL, about 430 mg/dL, about 440 mg/dL, about 450 mg/dL, about 460 mg/dL, about 470 mg/dL, about 480 mg/dL, about 490 mg/dL, about 500 mg/dL, about 510 mg/dL, about 520 mg/dL, about 530 mg/dL, about 540 mg/dL, about 550 mg/dL, about 560 mg/dL, about 570 mg/dL, about 580 mg/dL, about 590 mg/dL, about 600 mg/dL, about 610 mg/dL, about 620 mg/dL, about 630 mg/dL, about 640 mg/dL, and about 650 mg/dL. Each possibility represents a separate embodiment.

Within the scope of the present invention are hemoglobin A1c (HbA1c) levels after a single parenteral administration of the composition of the invention of between about 4% and about 10.5%, including each value within the specified range. For example, hemoglobin A1c (HbA1c) levels after a single parenteral administration include, but are not limited to about 4.0%, about 4.1%, about 4.2%, about 4.3%, about 4.4%, about 4.5%, about 4.6%, about 4.7%, about 4.8%, about 4.9%, about 5.0%, about 5.1%, about 5.2%, about 5.3%, about 5.4%, about 5.5%, about 5.6%, about 5.7%, about 5.8%, about 5.9%, about 6.0%, about 6.1%, about 6.2%, about 6.3%, about 6.4%, about 6.5%, about 6.6%, about 6.7%, about 6.8%, about 6.9%, about 7.0%, about 7.1%, about 7.2%, about 7.3%, about 7.4%, about 7.5%, about 7.6%, about 7.7%, about 7.8%, about 7.9%, about 8.0%, about 8.1%, about 8.2%, about 8.3%, about 8.4%, about 8.5%, about 8.6%, about 8.7%, about 8.8%, about 8.9%, about 9.0%, about 9.1%, about 9.2%, about 9.3%, about 9.4%, about 9.5%, about 9.6%, about 9.7%, about 9.8%, about 9.9%, about 10.0%, about 10.1%, about 10.2%, about 10.3%, about 10.4%, and about 10.5%. Each possibility represents a separate embodiment.

In addition, the present invention provides a method of treating obesity comprising the step of administering to a subject in need thereof a long-acting parenteral pharmaceutical composition comprising microparticles comprising dried water-in-oil-in-water (w/o/w) double emulsion droplets comprising an internal aqueous phase comprising a therapeutically effective amount of semaglutide or a pharmaceutically acceptable salt thereof; a water immiscible polymeric phase comprising a biodegradable carrier selected from the group consisting of polylactides, polyglycolides, polycaprolactones, and combinations thereof; and an external aqueous phase, wherein the composition is in depot form suitable for administration at a medically acceptable location in a subject in need thereof at a frequency of once every four weeks to once every six months.

The term "treating" as used herein with reference to obesity refers preventing weight gain, promoting weight loss, reducing excess body weight or treating obesity (e.g. by control of appetite, feeding, food intake, calorie intake, and/or energy expenditure), including morbid obesity, as well as associated diseases and health conditions including, but not limited to, obesity linked inflammation, obesity linked gallbladder disease and obesity induced sleep apnea.

In addition, the present invention provides a method of treating Parkinson's Disease comprising the step of administering to a subject in need thereof a long-acting parenteral pharmaceutical composition comprising microparticles comprising dried water-in-oil-in-water (w/o/w) double emulsion droplets comprising an internal aqueous phase comprising a therapeutically effective amount of semaglutide or a pharmaceutically acceptable salt thereof; a water immiscible polymeric phase comprising a biodegradable carrier selected from the group consisting of polylactides, polyglycolides, polycaprolactones, and combinations thereof; and an external aqueous phase, wherein the composition is in depot form suitable for administration at a medically acceptable location in a subject in need thereof at a frequency of once every four weeks to once every six months.

As used herein, the term "treating" with reference to Parkinson's Disease refers to reversing, alleviating, ameliorating, inhibiting, slowing down and/or stopping the progression or severity of at least one adverse effect or symptom of Parkinson's Disease including, for example, those associated with impaired motoric function.

It is understood that the amount of the semaglutide administered will be determined by a physician, according to various parameters including the chosen route of administration, the age, weight, and the severity of the patient's disease and symptoms. The required plasma concentrations of semaglutide that provide therapeutic efficacy can be determined, for example, from in-vitro and in-vivo models as is known in the art. According to some specific exemplary embodiments, the steady-state mean plasma concentration of semaglutide is between about 0.001 μg/ml and about 100 μg/ml, including each value within the specified range. According to other embodiments, the steady-state mean plasma concentration of semaglutide is between about 0.01 μg/ml and about 100 μg/ml, including each value within the specified range. According to further embodiments, the steady-state mean plasma concentration of semaglutide is between about 0.05 μg/ml and about 50 μg/ml, including each value within the specified range. According to additional embodiments, the steady-state mean plasma concentration of semaglutide is between about 0.05 μg/ml and about 10 μg/ml, including each value within the specified range. According to other embodiments, the steady-state mean plasma concentration of semaglutide is between about 0.1 μg/ml and about 1 μg/ml, including each value within the specified range.

According to further embodiments, the average plasma concentration of semaglutide is between about 1 ng/ml and about 100 μg/ml, including each value within the specified range. According to other embodiments, the average plasma concentration of semaglutide is between about 1 ng/ml and about 5,000 ng/ml, including each value within the specified range. According to yet other embodiments, the average plasma concentration of semaglutide is between about 1 ng/ml and about 1,000 ng/ml, including each value within the specified range. According to additional embodiments, the average plasma concentration of semaglutide is between about 1 ng/ml and about 500 ng/ml, including each value within the specified range. According to particular embodiments, the average plasma concentration of semaglutide is between about 1 ng/ml and about 300 ng/ml, including each value within the specified range. According to some embodiments, the average plasma concentration of semaglutide is between about 10 ng/ml and about 250 ng/ml, including each value within the specified range.

According to further embodiments, the compositions of the present invention provide equal or superior therapeutic efficacy to weekly injectable dosage forms of the semaglutide, with reduced incidence of side effects and/or with reduced severity of side effects. Each possibility represents a separate embodiment of the invention.

According to some embodiments, the parenteral pharmaceutical depot composition of this invention can be administered in vivo to a subject in need thereof. In some embodiments, the "subject" to which the depot composition is administered is a mammal, preferably, but not limited to, a human.

As used herein and in the appended claims, the term "about" refers to ±10%.

As used herein and in the appended claims, the singular forms "a", "an", and "the" include plural references unless the context clearly dictates otherwise. Thus, for example, reference to "a biodegradable carrier" includes a plurality of such carriers. It should be noted that the term "and" or the term "or" are generally employed in their sense including "and/or" unless the context clearly dictates otherwise.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1: Preparation of PLGA-based Injectable Semaglutide Microparticles

Semaglutide microspheres were prepared using water/oil/water (w1/o/w2) double emulsion solvent evaporation method according to the following exemplary procedure:

Internal water phase: 50 mg of semaglutide were hydrated by mixing with water (350 μl) followed by pH adjustment with NaOH to 7.8.

Organic phase: Methylene chloride was saturated with water at room temperature by mixing 50 ml of dichloromethane (DCM) and 5 ml water in a tightly closed bottle. Following phase separation after 30 minutes at room temperature, the bottom layer of water saturated DCM was used for the preparation of the organic phase. PLGA (Resomer® RG 502H Poly(D,L-lactide-co-glycolide) 50:50 acid terminated, MW 7-17,000; or Resomer® RG 502 Poly(D,L-lactide-co-glycolide) 50:50 ester terminated MW 7-17,000) was dissolved in the water saturated DCM.

External water phase: Sodium chloride and PVA were dissolved in 50 mL water to result in total concentrations of 0.25% PVA and 1.75% NaCl.

The internal water phase was then mixed into the PLGA-containing organic phase to form the w/o internal emulsion, using ultrasonic indenter (20 KHz, 20-30 sec., ~50 Watt, ice water bath) or a Polytron dispersing aggregate (12 mm, 20,000-30,000 rpm, 1 minute). The internal w/o emulsion was then mixed with the external water phase using high shear rotor-stator mixer (Polytron dispersing aggregate (12 mm, 11,000 rpm, 40 sec) or Caframo A231 straight mixer, 1,500 rpm, 2 minutes) at different temperatures to form the final w/o/w double emulsion. The obtained double emulsion was then kept in an open vessel with continuous stirring to allow evaporation of DCM and solidification of the peptide containing microparticles (MPs). Once solidification was completed, the suspension was centrifuged (3,000-5,000 rpm), sediment was washed with phosphate buffer (pH 7.4), centrifuged again, washed with water, collected using a small amount of pure water and dried on a Petri dish, protected from light, to obtain dry MPs. The MPs were collected and stored in tightly closed vials in a refrigerator.

Different semaglutide depot formulations and their preparation methods are detailed in Tables 1A-1I below. Microscopic images of representative microparticles are shown in FIGS. 1A-1L.

TABLE 1A

Semaglutide depot formulations MPS-01 to MPS-05

| Formulation | MPS-01 | MPS-02 | MPS-03 | MPS-04 | MPS-05 |
|---|---|---|---|---|---|
| | | | Internal water phase | | |
| Semaglutide 95.3%, mg | 51.0 | 50.6 | 50.0 | 50.2 | 50.2 |
| Semaglutide dry base, mg | 48.603 | 48.2218 | 47.67 | 47.84 | 47.84 |
| Water, μl | 359 | 350 | 353 | 390 | 356 |
| NaOH 1N, μl | 40 | 40 | 40 | 40 | 40 |
| | | | Oil phase | | |
| PLGA RG 502H, mg | 500 | 503 | 501 | 300 | |
| PLGA RG 502, mg | | | | | 500 |
| DCM, g | 4.6 | 4.632 | | | |
| water saturated DCM, g | | | 4.52 | 4.6 | 4.6 |
| DCM, ml | 3.47 | 3.50 | 3.41 | 3.47 | 3.47 |
| | | | External water phase | | |
| PVA | 50 ml 0.5% | 65 ml 0.5% | 50 ml 0.25% | 50 ml 0.25% | 50 ml 0.25% |
| NaCl | 0.5 g | 0.5 g | 1.75% | 1.75% | 1.75% |
| | | | Preparation | | |
| Sonication (indenter) 80W | 55% 4 × 10 sec on ice | 55% 4 × 10 sec on ice | 66% 2 × 15 sec RT | 66% 2 × 15 sec RT | 66% 2 × 15 sec RT |
| Process description | 100 ml beaker, Polytron 2100 12 mm 11,000 rpm 60 sec, evaporation overnight RT magnet | 100 ml beaker, magnet stirrer 12 mm max rpm 5 min, added 100 ml water overnight RT | 100 ml beaker, Polytron 2100 12 mm 11,000 rpm 20 sec, evaporation overnight RT magnet centrif. 5,000 rpm 2 × 5 min | 100 ml beaker, Polytron 2100 12 mm 11,000 rpm 20 sec, evaporation overnight RT magnet centrif. 5,000 rpm 2 × 5 min | 100 ml beaker, Polytron 2100 12 mm 11,000 rpm 20 sec, evaporation overnight RT magnet centrif. 5,000 rpm 2 × 5 min |
| | | | Characterization | | |
| Particle description | Spherical MPs 5-15 μm | Spherical MPs 10-40 μm, irregular shape | Spherical MPs 3-10 μm | Spherical MPs | |
| Binding (TNBS) | ~50% | ~75% | | | |

TABLE 1B

Semaglutide depot formulations MPS-06 to MPS-10

| Formulation | MPS-06 | MPS-07 | MPS-08 (Figure 1I) | MPS-09 | MPS-010 |
|---|---|---|---|---|---|
| | | | Internal water phase | | |
| Semaglutide 95.3%, mg | 50.6 | 50.2 | 50.6 | 50.1 | 50.3 |
| Semaglutide dry base, mg | 48.22 | 47.84 | 48.22 | 47.75 | 47.94 |
| Water, μl | 347 | 357 | 367 | 356 | 356 |
| NaOH 1N, μl | 40 | 40 | 40 | 40 | 40 |
| | | | Oil phase | | |
| PLGA RG 502H, mg | | 800 | | 500 | |
| PLGA RG 502, mg | 300 | | 800 | | 500 |
| water saturated DCM, g | 4.6 | 4.6 | 4.6 | 6 | 6 |
| DCM, ml | 3.47 | 3.47 | 3.47 | 4.53 | 4.53 |

TABLE 1B-continued

Semaglutide depot formulations MPS-06 to MPS-10

| Formulation | MPS-06 | MPS-07 | MPS-08 (Figure 1I) | MPS-09 | MPS-010 |
|---|---|---|---|---|---|
| External water phase | | | | | |
| PVA | 50 ml 0.25 | 50 ml 0.25% | 50 ml 0.25% | 50 ml 0.25% | 50 ml 0.25% |
| NaCl | 1.75% | 1.75% | 1.75% | 1.75% | 1.75% |
| Preparation | | | | | |
| Sonication (indenter) 80W | 66% 2 × 15 sec RT | 66% 2 × 15 sec ice water | 66% 2 × 15 sec ice water | 66% 2 × 15 sec ice water | 66% 2 × 15 sec ice water |
| Process description | 100 ml beaker, Polytron 2100 12 mm 11,000 rpm 20 sec, evaporation overnight RT magnet centrif. 5,000 rpm 2 × 5 min | 100 ml beaker, Polytron 2100 12 mm 11,000 rpm 20 sec, evaporation overnight RT magnet centrif. 3,000 rpm 10 min | 100 ml beaker, Polytron 2100 12 mm 11,000 rpm 20 sec, evaporation overnight RT magnet centrif. 3,000 rpm 10 min | 100 ml beaker, Polytron 2100 12 mm 11,000 rpm 20 sec, evaporation overnight RT magnet centrif. 3,000 rpm 10 min | 100 ml beaker, Polytron 2100 12 mm 11,000 rpm 20 sec, evaporation overnight RT magnet centrif. 3,000 rpm 10 min |

TABLE 1C

Semaglutide depot formulations MPS-11 to MPS-15

| Formulation | MPS-11 | MPS-12 | MPS-13 | MPS-14 | MPS-015 (Figure 1J) |
|---|---|---|---|---|---|
| Internal water phase | | | | | |
| Semaglutide 95.3%, mg | 50.1 | 50.2 | 50.0 | 50.0 | 50.0 |
| Semaglutide dry base, mg | 47.75 | 47.84 | 47.65 | 47.65 | 47.65 |
| Water, μl | 356 | 356 | 356 | 356 | 350 |
| NaOH 1N, μl | 40 | 40 | 40 | 40 | 40 |
| Sucrose 50% in water, μl | | | | 50 | |
| Oil phase | | | | | |
| PLGA RG 502H, mg | 200 | | 500 | | 500 |
| PLGA RG 502, mg | | 200 | | 450 | |
| water saturated DCM, g | 4.6 | 4.6 | 4.6 | 4.6 | 4.6 |
| DCM, ml | 3.47 | 3.47 | 3.47 | 3.47 | 3.47 |
| External water phase | | | | | |
| PVA | 50 ml 0.25% | 50 ml 0.25% | 50 ml 0.25% | 50 ml 0.25% | 50 ml 0.25% |
| NaCl | 1.75% | 1.75% | 1.75% | 1.75% | 1.75% |
| Preparation | | | | | |
| Sonication (indenter) 80W | 66% 2 × 15 sec ice water | 66% 2 × 15 sec ice water | 66% 2 × 15 sec ice water | 66% 2 × 15 sec ice water | 66% 2 × 15 sec ice water |
| Process description | 100 ml beaker, Polytron 2100 12 mm 11,000 rpm 40 sec, evaporation overnight RT magnet centrif. 3,000 rpm 10 minutes | 100 ml beaker, Polytron 2100 12 mm 11,000 rpm 40 sec, evaporation overnight RT magnet centrif. 3,000 rpm 10 minutes | 100 ml beaker, Polytron 2100 12 mm 11,000 rpm 40 sec, evaporation overnight RT magnet centrif. 3,000 rpm 10 minutes | 100 ml beaker, Polytron 2100 12 mm 11,000 rpm 40 sec, evaporation overnight RT magnet centrif. 3,000 rpm 10 minutes | 100 ml beaker, Polytron 2100 12 mm 11,000 rpm 40 sec, evaporation overnight RT magnet |

TABLE 1C-continued

Semaglutide depot formulations MPS-11 to MPS-15

| Formulation | MPS-11 | MPS-12 | MPS-13 | MPS-14 | MPS-015 (Figure 1J) |
|---|---|---|---|---|---|
| Characterization ||||||
| Particle description | spherical MPs 2-6 μm | spherical MPs 2-6 μm | | | |

TABLE 1D

Semaglutide depot formulations MPS-16 to MPS-19, MPS-21

| Formulation | MPS-16 | MPS-17 | MPS-18 | MPS-19 | MPS-21 |
|---|---|---|---|---|---|
| Internal water phase ||||||
| Semaglutide 95.3%, mg | 50.0 | 50.0 | 50.0 | 50 | 50.0 |
| Semaglutide dry base, mg | 47.65 | 47.65 | 47.65 | 48 | 47.65 |
| Water, μl | 350 | 350 | 350 | 350 | 350 |
| NaOH 1N, μl | 40 | 40 | 40 | 40 | 40 |
| PEG3350, mg | 50 | | 50 | 50 | 50 |
| Oil phase ||||||
| PLGA RG 502H, mg | | 500 | | 500 | 500 |
| PLGA RG 502, mg | 500 | | 500 | | |
| water saturated DCM, g | 4.6 | 4.6 | 4.6 | 4.6 | 4.6 |
| DCM, ml | 3.47 | 3.47 | 3.47 | 3.47 | 3.47 |
| External water phase ||||||
| PVA | | 50 ml 0.25% | 50 ml 0.25% | 50 ml 0.25% | 50 ml 0.25% |
| NaCl | | 1.75% | 1.75% | 1.75% | 1.75% |
| Preparation ||||||
| Sonication (indenter) 80W | | 66% 2 × 15 sec ice water | 66% 2 × 15 sec ice water | 66% 2 × 15 sec ice water | 66% 2 × 15 sec ice water |
| Process description | 100 ml beaker, Polytron 2100 12 mm 11,000 rpm 40 sec, evaporation overnight RT magnet | 100 ml beaker, Caframo straight A231 32 mm 1,500 rpm 2 minutes | 100 ml beaker, Caframo straight A231 32 mm 1,500 rpm 2 minutes | 100 ml beaker, Polytron 2100 12 mm 11,000 rpm 40 sec, evaporation overnight RT magnet | 100 ml beaker, Caframo straight A231 32 mm 1,500 rpm 2 minutes |

TABLE 1E

Semaglutide depot formulations MPS-22 to MPS-26M

| Formulation | MPS-22 | MPS-23 (FIG. 1A) | MPS-24 | MPS-25 (FIG. 1B) | MPS-26M |
|---|---|---|---|---|---|
| Internal water phase ||||||
| Semaglutide 95.3%, mg | 50.0 | 50.0 | 50.1 | 50.1 | 50.0 |
| Semaglutide dry base, mg | 47.65 | 47.65 | 47.75 | 47.75 | 47.65 |
| Water, μl | 350 | 350 | 350.00 | 350 | 350 |
| NaOH 1N, μl | 40 | 40 | 40 | 40 | 40 |
| PEG3350, mg | | | 55 | | |

TABLE 1E-continued

Semaglutide depot formulations MPS-22 to MPS-26M

| Formulation | MPS-22 | MPS-23 (FIG. 1A) | MPS-24 | MPS-25 (FIG. 1B) | MPS-26M |
|---|---|---|---|---|---|
| Oil phase | | | | | |
| PLGA RG 502H, mg | | 350 | | 500 | 300 |
| PLGA RG 502, mg | 350 | | 350 | | 500 |
| water saturated DCM, g | 4.6 | 4.6 | 4.6 | 6 | 4.6 |
| DCM, ml | 3.47 | 3.47 | 3.47 | 4.53 | 3.47 |
| External water phase | | | | | |
| PVA NaCl | 50 ml 0.25% 1.75% | 50 ml 0.25% 1.75% | 50 ml 0.25% 1.75% | 50 ml 0.25% 1.75% | 50 ml 0.25% 1.75% |
| Preparation | | | | | |
| Sonication (indenter) 80 W | 66% 2 × 15 sec ice water | 66% 2 × 15 sec ice water | 66% 2 × 15 sec ice water | 66% 2 × 15 sec ice water | 66% 2 × 15 sec ice water |
| Process description | 100 ml beaker, Polytron 2100 12 mm 11,000 rpm 40 sec, evaporation overnight RT magnet centrif. 3,000 rpm 10 min | 100 ml beaker, Polytron 2100 12 mm 11,000 rpm 40 sec, evaporation overnight RT magnet centrif. 3,000 rpm 10 min | 100 ml beaker, Polytron 2100 12 mm 11,000 rpm 40 sec, evaporation overnight RT magnet centrif. 3,000 rpm 10 min | 100 ml beaker, Polytron 2100 12 mm 11,000 rpm 20 sec, evaporation overnight RT magnet centrif. 3,000 rpm 10 min | 100 ml beaker, Polytron 2100 12 mm 11,000 rpm 40 sec, evaporation overnight RT magnet centrif. 3,000 rpm 10 min |
| Characterization | | | | | |
| Particle description | Spherical MPs 2-6 μm | Spherical MPs 2-6 μm | Spherical MPs 2-6 μm | | |

TABLE 1F

Semaglutide depot formulations MPS-27M to MPS-31M

| Formulation | MPS-27M (FIG. 1C) | MPS-28M | MPS-29M | MPS-30M | MPS-31M |
|---|---|---|---|---|---|
| Internal water phase | | | | | |
| Semaglutide 95.3%, mg | 50.0 | 50.0 | 50.0 | 50.0 | 50.0 |
| Semaglutide dry base, mg | 47.65 | 47.65 | 47.65 | 47.65 | 47.65 |
| Water, μl | 350 | 350 | 350 | 350 | 350 |
| NaOH 1N, μl | 40 | 40 | 40 | 40 | 40 |
| Oil phase | | | | | |
| PLGA RG 502H, mg | 100 | 100 | 200 | 250 | 250 |
| PLGA RG 502, mg | 400 | 400 | 300 | 250 | 250 |
| water saturated DCM, g | 4.6 | 6 | 6 | 6 | 4.6 |
| DCM, ml | 3.47 | 4.53 | 4.53 | 4.53 | 3.47 |
| External water phase | | | | | |
| PVA NaCl | 50 ml 0.25% 1.75% | 50 ml 0.25% 1.75% | 50 ml 0.25% 1.75% | 50 ml 0.25% 1.75% | 50 ml 0.25% 1.75% |

TABLE 1F-continued

Semaglutide depot formulations MPS-27M to MPS-31M

| Formulation | MPS-27M (FIG. 1C) | MPS-28M | MPS-29M | MPS-30M | MPS-31M |
|---|---|---|---|---|---|
| Preparation | | | | | |
| Sonication (indenter) 80 W | 66% 2 × 15 sec ice water | PT 30,000 rpm 60 sec ice water | PT 30,000 rpm 60 sec ice water | PT 20,000 rpm 60 sec ice water | PT 20,000 rpm 60 sec ice water |
| Process description | 100 ml beaker, Polytron 2100 12 mm 11,000 rpm 40 sec, evaporation overnight RT magnet centrif. 3,000 rpm 10 minutes | 100 ml beaker, Polytron 2100 12 mm 11,000 rpm 40 sec, evaporation overnight RT magnet centrif. 3,000 rpm 10 minutes | 100 ml beaker, Polytron 2100 12 mm 11,000 rpm 40 sec, evaporation overnight RT magnet centrif. 3,000 rpm 10 minutes | 100 ml beaker, Polytron 2100 12 mm 11,000 rpm 40 sec, evaporation overnight RT magnet centrif. 3,000 rpm 10 minutes | 100 ml beaker, Polytron 2100 12 mm 11,000 rpm 40 sec, evaporation overnight RT magnet centrif. 3,000 rpm 10 minutes |

TABLE 1G

Semaglutide depot formulations MPS-32S, MPS-33MS, MPS-34HL, MPS-35HL, MPS-36MLA

| Formulation | MPS-32S | MPS-33MS | MPS-34HL (FIG. 1D) | MPS-35HL | MPS-36MLA |
|---|---|---|---|---|---|
| Internal water phase | | | | | |
| Semaglutide 95.3%, mg | 50 | 50 | 50 | 50 | 50 |
| Semaglutide dry base, mg | 47.65 | 47.65 | 47.65 | 47.65 | 47.65 |
| Water, μl | 350 | 350 | 350 | 350 | 350 |
| NaOH 1N, μl | 40 | 40 | 40 | 40 | 40 |
| Oil phase | | | | | |
| PLGA RG 502H, mg | | 100 | 500 | 500 | 400 |
| PLGA RG 502, mg | 500 | 400 | | | |
| PLA R-202H, mg | | | | | 100 |
| Stearic acid, mg | 20 | 20 | | | |
| Hydrog. lecithin Lipoid S 100-3, mg | | | 10 | 50 | |
| water saturated DCM, g | 6.3 | 6 | 6 | 6 | 6 |
| DCM, ml | 4.75 | 4.53 | 4.53 | 4.53 | 4.53 |
| External water phase | | | | | |
| PVA NaCl | 50 ml 0.25% 1.75% | 50 ml 0.25% 1.75% | 50 ml 0.25% 1.75% | 50 ml 0.25% 1.75% | 50 ml 0.25% 1.75% |
| Preparation | | | | | |
| Sonication (indenter) 80 W | PT 20,000 rpm 60 sec ice water cold generator | PT 20,000 rpm 60 sec ice water cold generator | 66% 3 × 15 sec ice water | 66% 3 × 15 sec ice water | PT 25,000 rpm 120 sec ice water cold generator |
| Process description | 100 ml beaker, Polytron 2100 12 mm | 100 ml beaker, Polytron 2100 12 mm | 100 ml beaker, Polytron 2100 12 mm | 100 ml beaker, Polytron 2100 12 mm | 100 ml beaker, Polytron 2100 12 mm |

TABLE 1G-continued

Semaglutide depot formulations MPS-32S,
MPS-33MS, MPS-34HL, MPS-35HL, MPS-36MLA

| Formulation | MPS-32S | MPS-33MS | MPS-34HL (FIG. 1D) | MPS-35HL | MPS-36MLA |
|---|---|---|---|---|---|
| | 11,000 rpm 40 sec, evaporation overnight RT magnet centrif. 3,000 rpm 10 minutes | 11,000 rpm 40 sec, evaporation overnight RT magnet centrif. 3,000 rpm 10 minutes | 11,000 rpm 40 sec, evaporation overnight RT magnet centrif. 3,000 rpm 10 minutes | 11,000 rpm 40 sec, evaporation overnight RT magnet centrif. 3,000 rpm 10 minutes | 11,000 rpm 40 sec, evaporation overnight RT magnet centrif. 3,000 rpm 10 minutes |

TABLE 1H

Semaglutide depot formulations MPS-37MLA,
MPS-38H, MPS-39H, MPS-40, MPS-41

| Formulation | MPS-37MLA | MPS-38H | MPS-39H | MPS-40 (FIG. 1E) | MPS-41 (FIG. 1F) |
|---|---|---|---|---|---|
| Internal water phase | | | | | |
| Semaglutide 95.3%, mg | 50 | 30 | 30 | 30 | 30 |
| Semaglutide dry base, mg | 47.65 | 28.59 | 28.59 | 28.59 | 28.59 |
| Water, μl | 350 | 250 | 250 | 250 | 250 |
| NaOH 1N, μl | 40 | 25 | 25 | 25 | 25 |
| Oil phase | | | | | |
| PLGA RG 502H, mg | 300 | 500 | 800 | 500 | 500 |
| PLGA RG 502, mg | | | | | 300 |
| PLA R-202H, mg | 200 | | | | |
| water saturated DCM, g | 6 | 4.6 | 6 | 4.6 | 6 |
| DCM, ml | 4.53 | 3.47 | 4.53 | 3.47 | 4.53 |
| External water phase | | | | | |
| PVA NaCl | 50 ml 0.25% 1.75% | 50 ml 0.25% 1.75% | 50 ml 0.25% 1.75% | 50 ml 0.25% 1.75% | 50 ml 0.25% 1.75% |
| Preparation | | | | | |
| Sonication (indenter) 80 W | PT 25,000 rpm 120 sec ice water cold generator | PT 25,000 rpm 120 sec ice water cold generator | PT 25,000 rpm 120 sec ice water cold generator | Branson 30% 2 × 15 sec ice water | Branson 30% 2 × 15 sec ice water |
| Process description | 100 ml beaker, Polytron 2100 12 mm 11,000 rpm 40 sec, evaporation overnight RT magnet centrif. 3,000 rpm 10 minutes | 100 ml beaker, Polytron 2100 12 mm 11,000 rpm 40 sec, evaporation overnight RT magnet centrif. 3,000 rpm 10 minutes | 100 ml beaker, Polytron 2100 12 mm 11,000 rpm 40 sec, evaporation overnight RT magnet centrif. 3,000 rpm 10 minutes | ice bath, 100 ml beaker, Polytron 2100 12 mm 11,000 rpm 40 sec, evaporation overnight RT magnet centrif. 3,000 rpm 10 minutes | ice bath, 100 ml beaker, Polytron 2100 12 mm 11,000 rpm 40 sec, evaporation overnight RT magnet centrif. 3,000 rpm 10 minutes |

TABLE 1I

Semaglutide depot formulations MPS-42 to MPS-46

| Formulation | MPS-42 | MPS-43 (FIG. 1G) | MPS-44 (FIG. 1H) | MPS-45 (FIG. 1K) | MPS-46 (FIG. 1L) |
|---|---|---|---|---|---|
| Internal water phase | | | | | |
| Semaglutide 95.3%, mg | 30 | 50 | 30 | 50 | 50 |
| Semaglutide dry base, mg | 28.59 | 47.65 | 28.59 | 47.65 | 47.65 |
| Water, μl | 250 | | | 350 | 350 |
| PVA 0.1% in water, μl | | 350 | 250 | | |
| NaOH 1N, μl | 25 | 40 | 25 | 40 | 40 |
| Oil phase | | | | | |
| PLGA RG 502H, mg | 500 | 500 | 500 | 350 | 500 |
| Hydrog. lecithin Lipoid S 100-3, mg | 16 | | | | 11 |
| water saturated DCM, g | 4.6 | 4.6 | 4.6 | 4.6 | 6 |
| DCM, ml | 3.47 | 3.47 | 3.47 | 3.47 | 4.53 |
| External water phase | | | | | |
| PVA | 50 ml 0.25% | 50 ml 0.25% | 50 ml 0.25% | 50 ml 0.25% | 50 ml 0.25% |
| NaCl | 1.75% | 1.75% | 1.75% | 1.75% | 1.75% |
| Preparation | | | | | |
| Sonication (indenter) 80 W Process description | Branson 30% 3 × 15 sec ice water ice bath, 100 ml beaker, Polytron 2100 12 mm 11,000 rpm 40 sec, evaporation overnight RT magnet centrif. 3,000 rpm 10 minutes | Branson 30% 2 × 15 sec ice water ice bath, 100 ml beaker, Polytron 2100 12 mm 11,000 rpm 40 sec, evaporation overnight RT magnet centrif. 3,000 rpm 10 minutes | Branson 30% 2 × 15 sec ice water ice bath, 100 ml beaker, Polytron 2100 12 mm 11,000 rpm 40 sec, evaporation overnight RT magnet centrif. 3,000 rpm 10 minutes | Branson 30% 2 × 15 sec ice water ice bath, 100 ml beaker, Polytron 2100 12 mm 11,000 rpm 40 sec, evaporation overnight RT magnet centrif. 3,000 rpm 10 minutes | Branson 30% 2 × 15 sec ice water ice bath, 100 ml beaker, Polytron 2100 12 mm 11,000 rpm 40 sec, evaporation overnight RT magnet centrif. 3,000 rpm 10 minutes |

Example 2: In-Vitro Release Profiles

The in-vitro release profiles of the depot formulations prepared according to Example 1 were measured. Due to the instability of semaglutide in the release medium, semaglutide release from microparticles was performed using a separate tube for each time point with a high MPs : release medium ratio.

15 mg of MPs loaded with semaglutide were placed in 3 ml of 0.1M phosphate buffer, pH 7.4, containing 0.2% BSA and 0.05% sodium azide. Shaker speed was set at ~100 strokes per minute. Release experiments were carried out at a ratio of 15 mg MPs per 3 ml of the buffer. After 3 weeks of the release, the buffer was replaced with the same medium, additionally containing 200 μg/ml of porcine pancreas lipase.

The release rate was determined by assessing the amount of semaglutide which remained in the MPs at predetermined time points. The semaglutide was extracted from the microparticles and separated from the residue by centrifugation. The clear supernatant was transferred into a spectrophotometer cell and analyzed for semaglutide content using UV calibration curve for 2-points (293-350 nm) method, based on the first derivative calibration curve. Alternatively, samples were tested by HPLC.

The determination of semaglutide burst in the supernatant after 24 hours release was determined as follows: Release vials were placed into a centrifuge at 3,600 rpm for 12 minutes. 1.5 ml of supernatant were transferred into a 2 ml Eppendorf tube at 10,000 rpm for 8 min. 1 ml of the supernatant was placed into a spectrophotometer cell and analyzed for semaglutide content using UV calibration curve for 2-points (293-350 nm) method, based on the first derivative of the spectral calibration curve.

Figure 2:
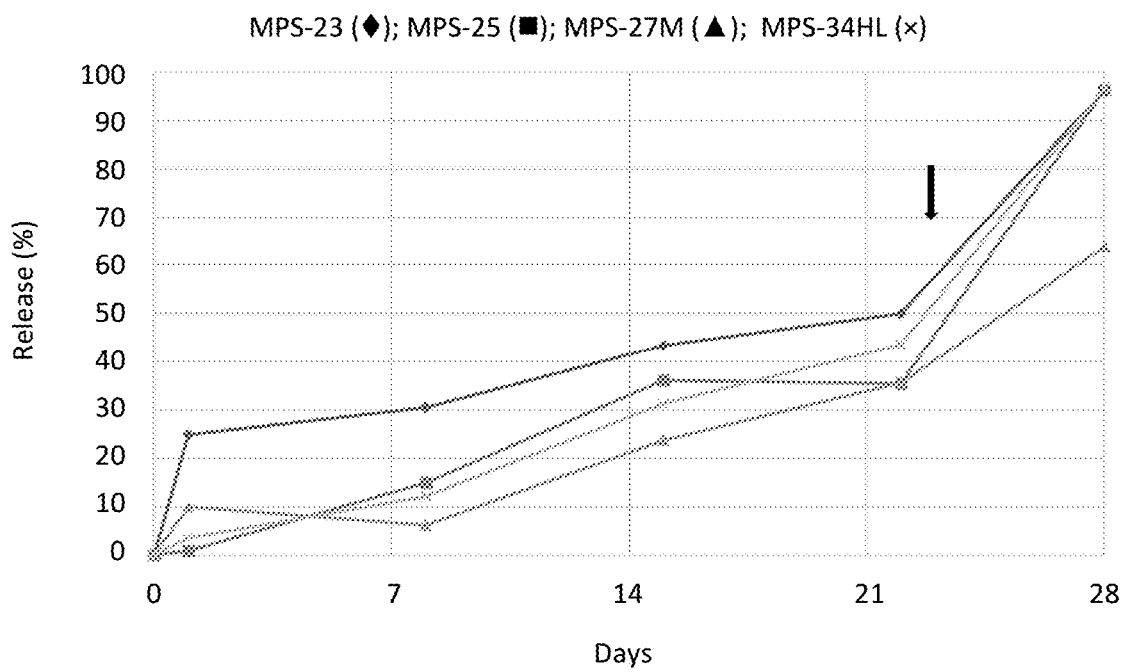
FIG. 2: shows the in vitro release of semaglutide from depot formulations MPS-23 (♦); MPS-25 (■); MPS-27M (▲); and MPS-34HL (×). The arrow indicates the time point at which porcine pancreas lipase (PPL) was added.
Figure 3:
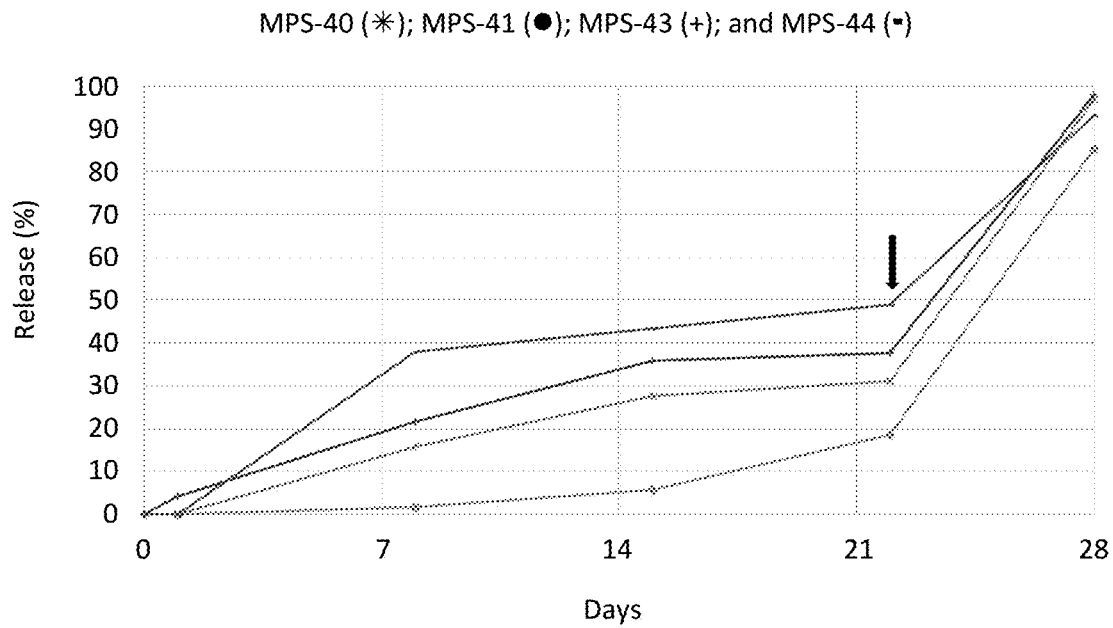
FIG. 3: shows the in vitro release of semaglutide from depot formulations MPS-40 (✳); MPS-41 (●); MPS-43 (+); and MPS-44 (▬). The arrow indicates the time point at which porcine pancreas lipase (PPL) was added.
Figure 4A:
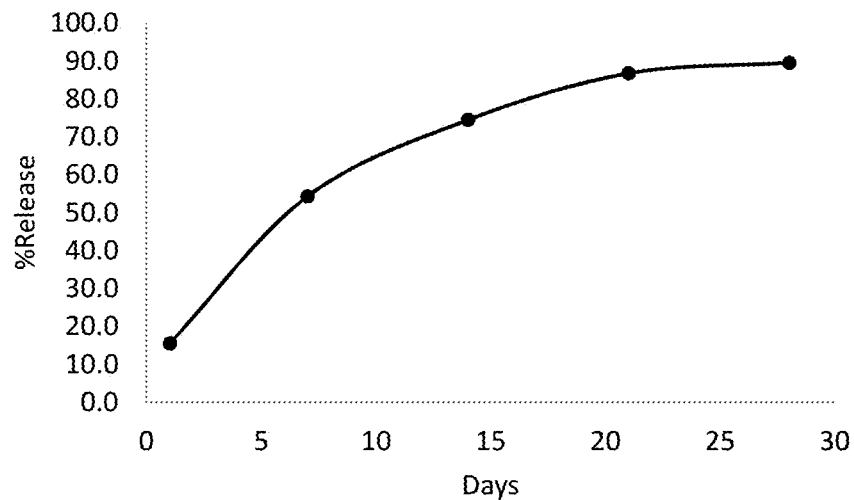
FIGS. 4A-4B.
Figure 4B:
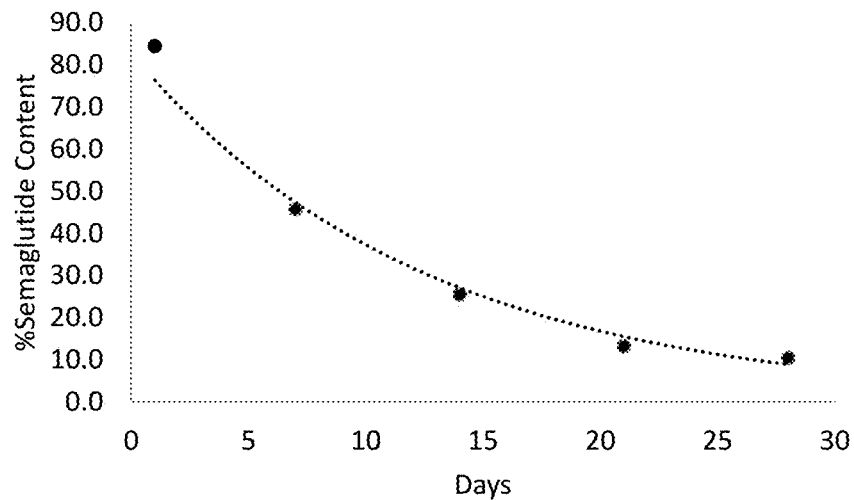

The release profiles of several formulations are shown in FIGS. 2-3. FIG. 4A shows the release profile of semaglutide from the MPS-46 depot formulation and FIG. 4B shows the semaglutide content (%) in the MPs during the release. The results are summarized in Table 2.

TABLE 2

Release of semaglutide from depot formulation MPS-46

| Day | MPs-46% in MPs | | | % Release |
| | Result 1 | Result 2 | Average | 100-Average |
| --- | --- | --- | --- | --- |
| 1 | 84.91 | 84.00 | 84.5 | 15.5 |
| 7 | 47.24 | 44.11 | 45.7 | 54.3 |
| 14 | 26.57 | 24.43 | 25.5 | 74.5 |
| 21 | 13.20 | 13.25 | 13.2 | 86.8 |
| 28 | 10.48 | 10.34 | 10.4 | 89.6 |

Example 3: Effect of Divalent Ions and Porcine Pancreas Lipase on the Release of Semaglutide From the MPs Microparticles loaded with semaglutide were washed with divalent ions ($Mg^{2+}$ or $Zn^{2+}$) and the release of semaglutide from the microparticles was determined as detailed in Example 2. The results are summarized in Table 3.

TABLE 3

Burst release of semaglutide from MPs washed with divalent ions

| | Semaglutide per 15 mg dry MPs [µg] | Burst in 3 ml 0.1M phosphate buffer, pH 7.4 [µg/ml] |
| --- | --- | --- |
| MPs-09 microparticles | 1214 | 137 |
| MPs-09 washed with 2% $MgSO_4$ and water | 1255 | 74 |
| MPs-09 washed with 2% Zn acetate and water | 1086 | 77 |

The results indicate that washing with solution of divalent cations decreases the initial burst.

The effect of Porcine Pancreas Lipase (PPL) on the release of semaglutide from the microparticles was tested. The results are summarized in Table 4. Interaction of MPs with PPL demonstrated that different formulations have different sensitivity to PPL as follows: combination of Resomers® 502 and 502H was found to be less sensitive to PPL hydrolysis (MPs-27 and 41) while MPs composed of Resomer® 502H alone degraded faster (MPs-34). Also, degradation in the presence of PPL was not dependent on the concentration of the enzyme for pure Resomer® 502H MPs but may be sensitive to enzyme concentration in mixtures of the polymers.

TABLE 4

Release of semaglutide from MPs in the presence of PPL

| Formulation | Initial (T = 0) | Day 15, No lipase | Day 15, 75 µg lipase at day 8 | Day 15, 300 µg lipase at day 8 |
| --- | --- | --- | --- | --- |
| MPs-27 | 1371 | 1045 (76.2%) | 1206 (80%) | 1043 (76.1%) |
| MPs-34 | 1299 | 893 (68.7%) | 598 (46.0%) | 607 (46.7%) |
| MPs-41 | 515 | 476 (92.4%) | 355 (68.9%) | 364 (70.7%) |

Example 4: Comparison of Semaglutide Formulations in an Animal Model of Diabetes The objective of this study was to test the pharmacokinetic and pharmacodynamic effect of various formulations of semaglutide in genetically diabetic male db/db mice.

Treatment Groups:
1. Naïve control normal mice (n=10)
2. Placebo (vehicle) control (n=10)
3. Semaglutide API dose 0.06 mg/kg/day for 28 days, SC (n=10)
4. Semaglutide API dose 0.4 mg/kg/day for 28 days, SC (n=10)
5. Semaglutide depot dose 2 mg/kg (API based) once on Day-1 only: 25 mg/kg, IM (n=10)

Formulation Preparation:
SEMA-031120, 25.3 mg/kg: 25.3 mg of semaglutide depot formulation was dissolved in 1.0 ml of water for injection and was used immediately.
Stock solution A: 10.0 mg of semaglutide API was dissolved in 25.0 ml of water for injection and the solution (termed stock solution A) was used for one week, and stored in a refrigerator at 2-8° C.
S-API: 0.06 mg/kg dose: 1.5 ml of stock solution A was transferred to a 10 ml volumetric flask and diluted with water to a concentration of 0.06 mg/ml. Fresh solution was prepared every week and was stored in a refrigerator at 2-8° C.
S-API: 0.4 mg/kg dose: Stock solution A was used as is. As detailed above, the solution was prepared every week and stored in a refrigerator at 2-8° C.

Study Protocol:
Male db/db mice (10-12 weeks old) from Jackson Laboratory were fed on rodent chow diet throughout study duration.
On Day-1, ad-lib fed blood glucose was recorded using a glucometer and body weight was determined using an animal weighing balance. Blood samples were collected for the measurement of HbA1c levels.
Based on blood glucose, body weight and HbA1c levels, animals were grouped into different treatment groups as detailed above.
Animals from Group 2 to 4 were treated daily with their respective treatments for 28 days (Dose volume: 1 ml/kg) by subcutaneous route (SC).
Animals from Group 5 were treated with the semaglutide depot formulation on Day-1 only (Dose volume: 1 ml/kg) by intramuscular injection.
Ad lib fed blood glucose levels were recorded every third day throughout the study period i.e. on Day-1, Day-3, Day-6, Day-9, Day-12, Day-15, Day-18, Day-21, Day-24, and Day-27. Samples were collected 3h post treatment.
On Day-14 and Day-28, blood glucose levels were monitored in overnight fasted animals (~14-16 h).
Semaglutide depot formulation (Group 5): plasma samples for the measurement of test compound levels by bioanalysis were collected on Day-1, Day-7, Day-14, Day-21, Day-28, Day-35, Day-42, Day-49 and Day-56.

Semaglutide-API: Samples for the measurement of Semaglutide-API levels by bioanalysis were collected on Day-1, Day-7, Day-14, Day-21 and Day-28 at 0 h (before treatment) and 3 h post treatment.

On Day-0 and Day-28, blood samples were collected for the measurement of HbA1c levels.

Body weight and feed intake were recorded every day throughout the treatment period.

At each time point, approximately 100 µl of blood was withdrawn from retroorbital plexus of each animal into labeled tubes containing Li-heparin (10 IU/ml of blood). The tubes were mixed by manual inversion 4 to 5 times. The blood samples were always kept on cold ice and the plasma was separated by centrifugation within 30 minutes from sample collection. Plasma was separated by centrifuging the blood sample at 5,000 rpm for 5 minutes at 2-8° C. The plasma samples were stored at -80 ° C. until bioanalysis.

Results:

Effect of Test Formulations on Ad-Lib Fed Blood Glucose in db/db Mice:

db/db mice had significantly higher blood glucose levels as compared to normal mice. Semaglutide API at 0.06 and 0.4 mg/kg/day doses showed significant reduction in ad-lib fed blood glucose levels as compared to vehicle control. Semaglutide depot at 25 mg/kg (dose 2 mg/kg, API based), IM, once on Day-1 only, showed significant reduction in ad-lib fed blood glucose levels as compared to vehicle control.

Figure 5:
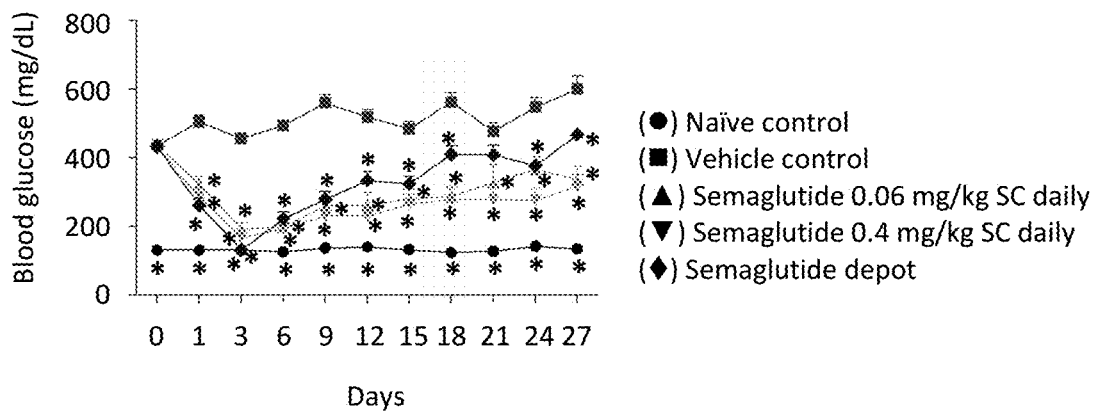
FIG. 5: shows the ad-lib fed blood glucose levels in Groups 1—Naïve control (●); Group 2—Vehicle control (■); Group 3—semaglutide 0.06 mg/kg SC daily (▲); Group 4—semaglutide 0.4 mg/kg SC daily (▼); and Group 5—semaglutide depot (♦). Data is shown as mean+SEM, * p<0.05 against Vehicle. One Way ANOVA followed by Dunnett's test.

The results are shown in FIG. 5 and summarized in Table 5.

TABLE 5

| Mean glucose (upper row); SD (middle row); SEM (bottom row) [mg/dL] | | | | | | | | | | |
|---|---|---|---|---|---|---|---|---|---|---|
| Group | Day 0 | Day 1 | Day 3 | Day 6 | Day 9 | Day 12 | Day 15 | Day 18 | Day 21 | Day 24 | Day 27 |
| 1 | 131.1 | 132.3 | 131.3 | 126.3 | 137.5 | 140.0 | 132.5 | 125.3 | 127.6 | 142.6 | 134.8 |
|  | 12.01 | 15.63 | 23.57 | 13.10 | 15.79 | 13.83 | 14.39 | 16.01 | 16.18 | 27.59 | 10.79 |
|  | 3.80 | 4.94 | 7.45 | 4.14 | 4.99 | 4.37 | 4.55 | 5.06 | 5.12 | 8.73 | 3.41 |
| 2 | 434.8 | 505.9 | 455.7 | 494.5 | 560.3 | 519.5 | 483.4 | 563.2 | 477.3 | 548.1 | 600.6 |
|  | 56.20 | 58.98 | 52.01 | 46.57 | 76.53 | 67.44 | 67.01 | 81.95 | 79.43 | 87.85 | 121.8 |
|  | 17.77 | 18.65 | 16.45 | 14.73 | 24.20 | 21.33 | 21.19 | 25.92 | 25.12 | 27.78 | 38.52 |
| 3 | 434.5 | 324.3 | 191.0 | 199.7 | 260.1 | 262.0 | 280.9 | 287.5 | 328.5 | 366.3 | 336.3 |
|  | 51.66 | 67.44 | 59.50 | 95.58 | 117.9 | 113.4 | 90.76 | 94.28 | 157.8 | 116.3 | 124.2 |
|  | 17.77 | 21.33 | 18.81 | 30.23 | 37.29 | 35.84 | 28.70 | 29.81 | 49.91 | 36.77 | 39.28 |
| 4 | 430.7 | 287.2 | 166.7 | 195.3 | 230.7 | 230.8 | 265.9 | 278.6 | 278.7 | 275.9 | 318.0 |
|  | 54.28 | 68.04 | 80.71 | 65.23 | 131.1 | 77.01 | 87.77 | 95.79 | 94.24 | 105.6 | 100.6 |
|  | 17.16 | 21.52 | 25.52 | 20.63 | 43.70 | 25.67 | 29.26 | 31.93 | 31.41 | 35.20 | 33.53 |
| 5 | 433.7 | 261.5 | 132.3 | 222.4 | 279.1 | 334.0 | 325.5 | 410.1 | 409.6 | 377.9 | 467.0 |
|  | 50.26 | 69.87 | 25.20 | 61.61 | 74.91 | 80.65 | 63.62 | 80.10 | 88.88 | 35.31 | 49.25 |
|  | 15.89 | 22.09 | 7.97 | 19.48 | 23.69 | 25.50 | 20.12 | 25.33 | 28.11 | 11.17 | 15.58 |

Figure 6:
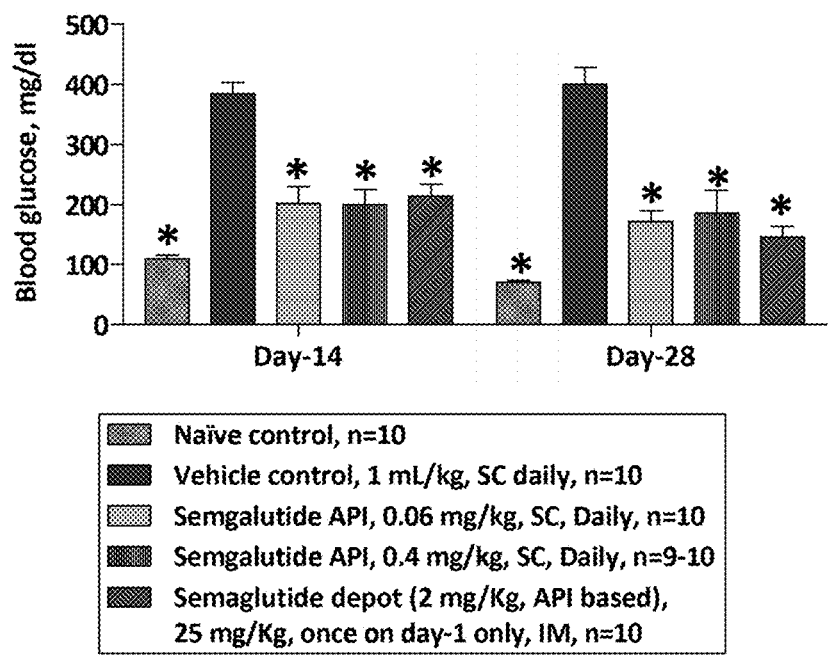
FIG. 6: shows the fasting blood glucose levels at days 14 and 28. Data is shown as mean+SEM, * p<0.05 against Vehicle. One Way ANOVA followed by Dunnett's test.

Effect of Test Formulations on Fasting Blood Glucose in db/db Mice:

db/db mice had significantly higher fasting blood glucose levels as compared to normal mice. Semaglutide API at 0.06 and 0.4 mg/kg/day doses showed significant reduction in fasting blood glucose levels on Day-14 and Day-28 as compared to vehicle control. Semaglutide depot at 25 mg/kg (dose 2 mg/kg, API based), IM, once on Day-1 only, showed significant reduction in fasting blood glucose levels on Day-14 and Day-28 as compared to vehicle control. The results are shown in FIG. 6 and summarized in Table 6.

TABLE 6

| | Mean glucose (upper row); SD (middle row); SEM (bottom row) [mg/dL] | | | |
|---|---|---|---|---|
| | Day 14 | | Day 28 | |
| Group | Pre-dose | 3 hrs post-dose | Pre-dose | 3 hrs post-dose |
| 1 | 116.7 | 109.5 | 66.7 | 70.1 |
|  | 22.26 | 18.53 | 10.31 | 10.69 |
|  | 7.04 | 5.86 | 3.26 | 3.38 |
| 2 | 352.5 | 384.3 | 355.2 | 399.7 |
|  | 93.83 | 57.93 | 76.77 | 89.16 |
|  | 29.67 | 18.32 | 24.28 | 28.19 |
| 3 | 308.1 | 201.4 | 159.8 | 171.2 |
|  | 73.95 | 89.23 | 50.64 | 57.57 |
|  | 23.39 | 28.22 | 16.01 | 18.21 |
| 4 | 291.67 | 200.0 | 161.56 | 185.89 |
|  | 131.49 | 74.51 | 54.89 | 113.86 |
|  | 43.83 | 24.84 | 18.30 | 37.95 |
| 5 | 223.2 | 213.3 | 166.3 | 145.7 |
|  | 61.10 | 65.21 | 38.99 | 55.32 |
|  | 19.32 | 20.62 | 12.33 | 17.49 |

Figure 7:
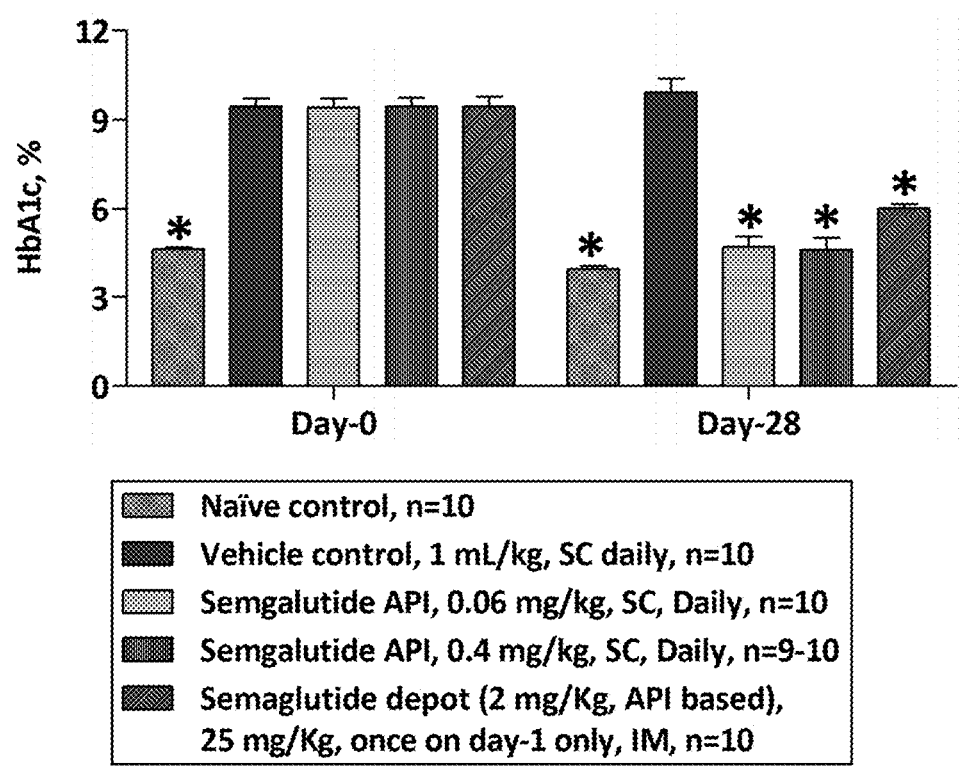
FIG. 7: shows the HbA1c in db/db mice at days 0 and 28. Data is shown as mean+SEM, * p<0.05 against Vehicle. One Way ANOVA followed by Dunnett's test.

Effect of Test Formulations on HbA1c in db/db Mice:

db/db mice had significantly higher HbA1c levels as compared to normal mice. Semaglutide API at 0.06 and 0.4 mg/kg/day doses showed significant reduction in HbA1c levels on Day-28 as compared to vehicle control. Semaglutide depot at 25 mg/kg (dose 2 mg/kg, API based), IM, once on Day-1 only, showed significant reduction in HbA1c levels on Day-28 as compared to vehicle control. The results are shown in FIG. 7 and summarized in Table 7.

TABLE 7

| | Mean HbA1c (upper row); SD (middle row); SEM (bottom row) [%] | |
|---|---|---|
| Group | Day 0 | Day 28 |
| 1 | 4.61 | 3.95 |
|  | 0.19 | 0.32 |
|  | 0.06 | 0.10 |
| 2 | 9.44 | 9.92 |
|  | 0.82 | 1.43 |
|  | 0.26 | 0.45 |

TABLE 7-continued

| | Mean HbA1c (upper row); SD (middle row); SEM (bottom row) [%] | |
|---|---|---|
| Group | Day 0 | Day 28 |
| 3 | 9.40 | 4.69 |
| | 0.95 | 1.11 |
| | 0.30 | 0.35 |
| 4 | 9.44 | 4.59 |
| | 0.89 | 1.23 |
| | 0.28 | 0.41 |
| 5 | 9.45 | 6.01 |
| | 1.00 | 0.45 |
| | 0.32 | 0.14 |

Figure 8:
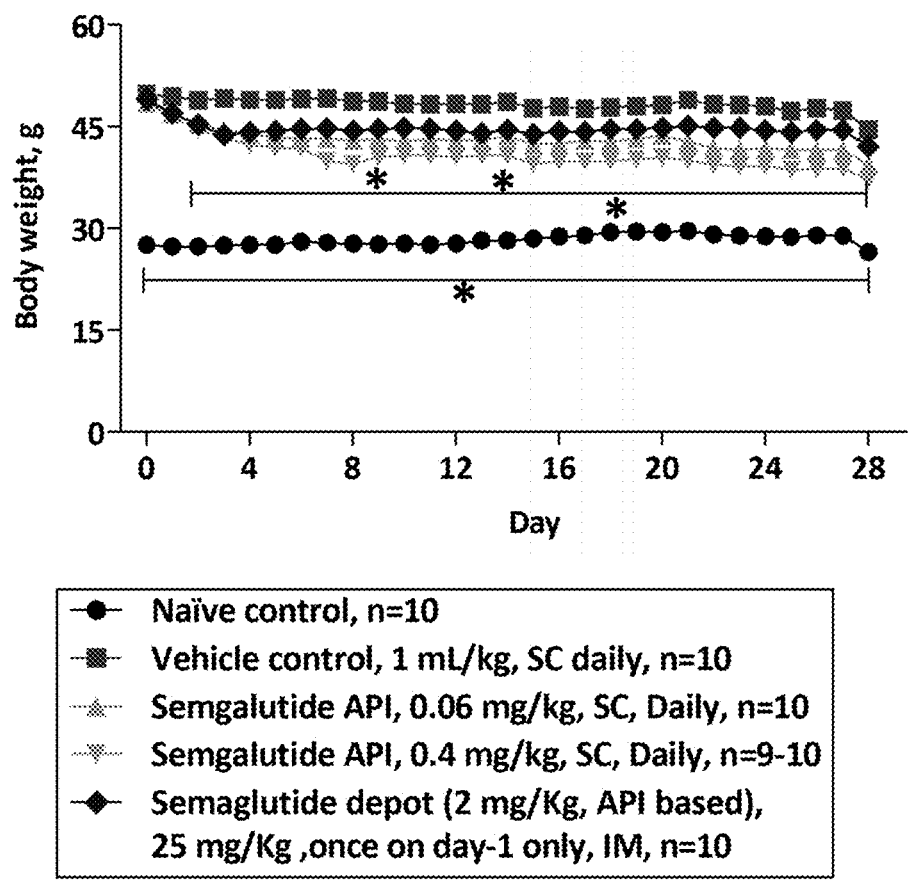
FIG. 8: shows the body weight in db/db mice in Groups 1—Naïve control (●); Group 2—Vehicle control (■); Group 3—semaglutide 0.06 mg/kg SC daily (▲); Group 4—semaglutide 0.4 mg/kg SC daily (▼); and Group 5—semaglutide depot (◆).
Figure 9A:
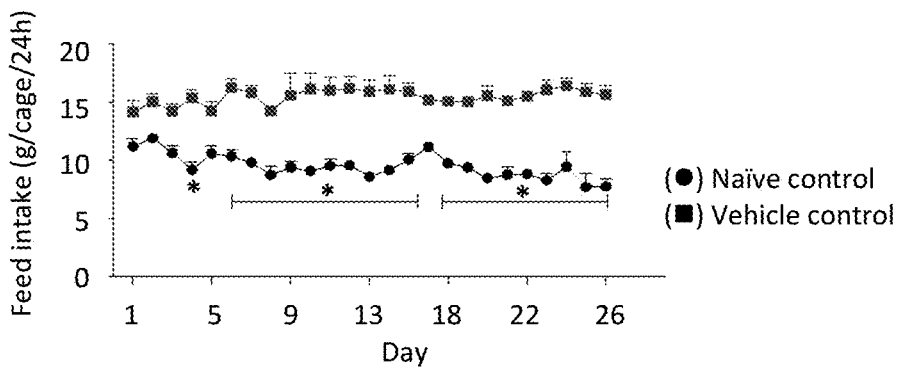
FIGS. 9A-9D: show the feed intake.
Figure 9B:
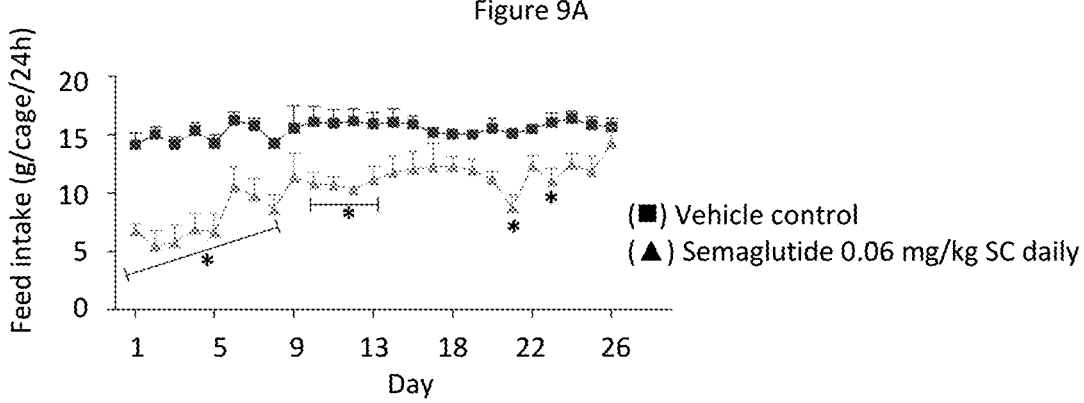
Figure 9C:
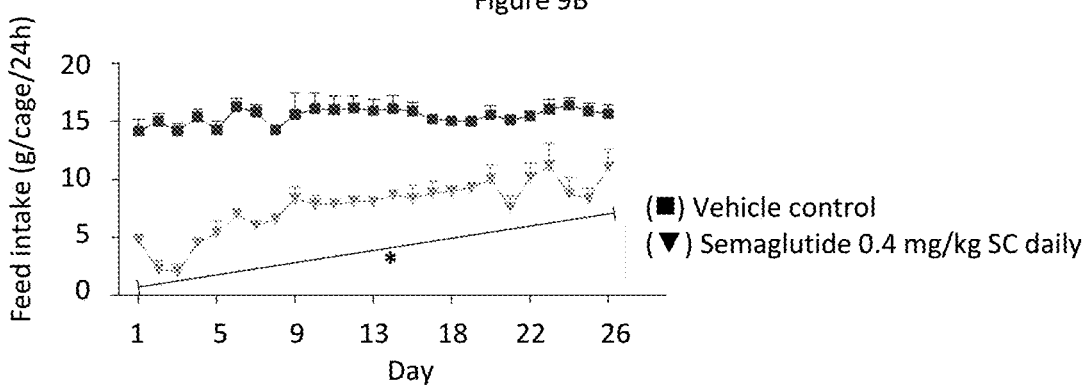
Figure 9D:
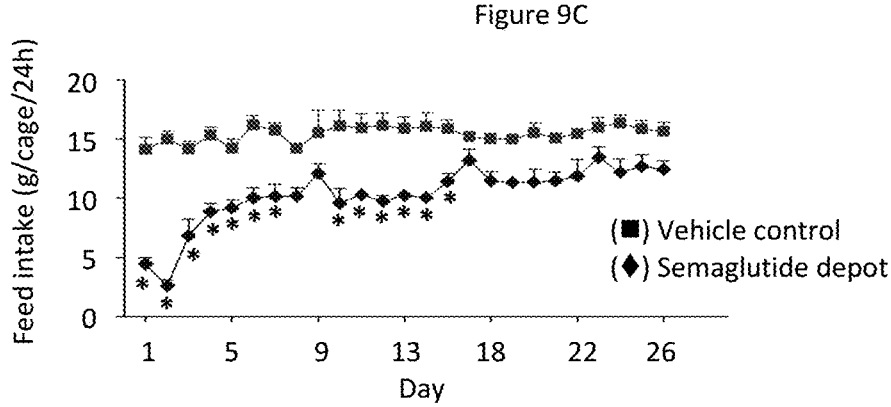
Figure 10A:
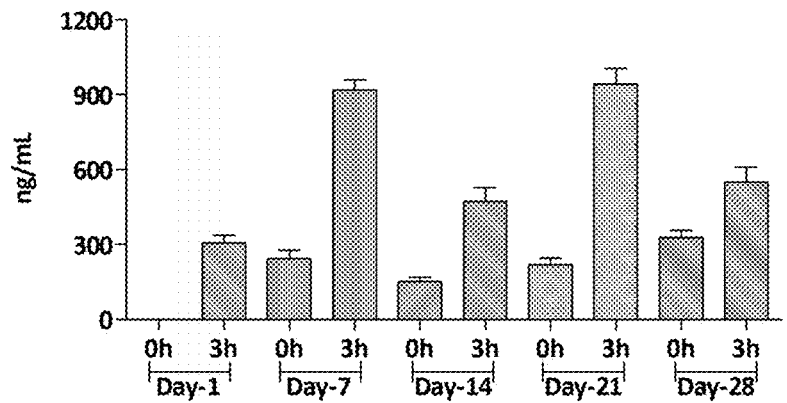
FIGS. 10A-10D: show semaglutide plasma concentrations in db/db mice.
Figure 10B:
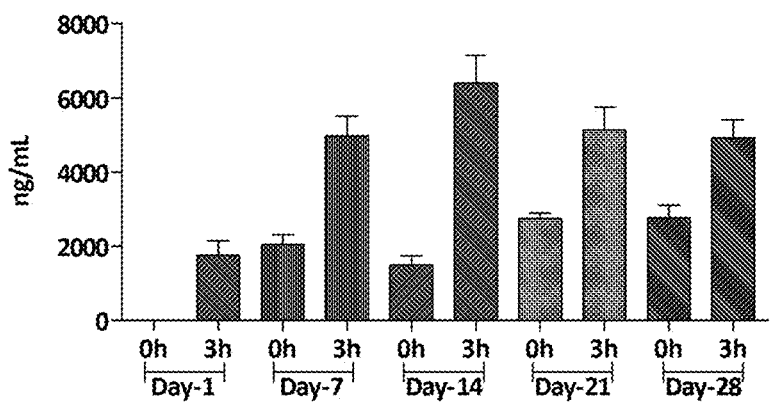
Figure 10C:
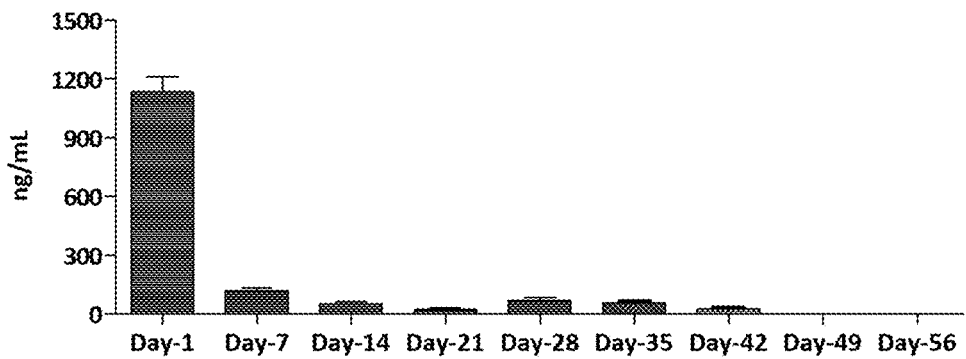
Figure 10D:
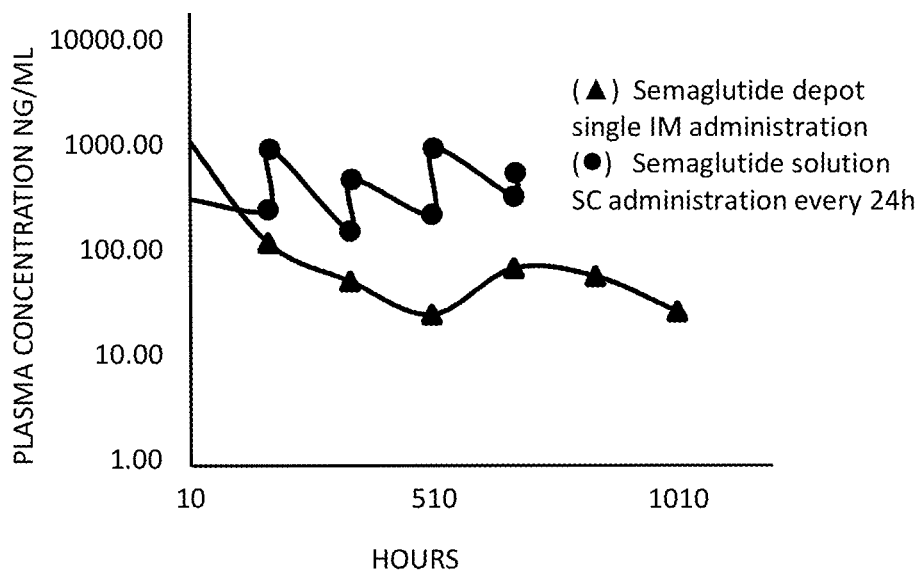

Effect of Test Formulations on Body Weight in db/db Mice:

db/db mice had significantly higher body weights as compared to normal mice. Semaglutide API at 0.06 and 0.4 mg/kg/day doses showed significant reduction in body weights as compared to vehicle control. Semaglutide depot at 25 mg/kg (dose 2 mg/kg, API based), IM, once on Day-1 only, showed significant reduction in body weights as compared to vehicle control. The results are shown in FIG. 8 and summarized in Table 8.

TABLE 8

| | Mean body weight (upper row); SD (middle row); SEM (bottom row) [g] | | | | | | | | | |
|---|---|---|---|---|---|---|---|---|---|---|
| Group | Day 0 | Day 1 | Day 3 | Day 6 | Day 9 | Day 12 | Day 15 | Day 18 | Day 21 | Day 24 | Day 27 |
| 1 | 27.66 | 27.32 | 27.56 | 28.06 | 27.71 | 27.84 | 28.47 | 29.48 | 29.69 | 28.82 | 28.95 |
| | 1.65 | 1.48 | 1.51 | 1.39 | 1.42 | 1.40 | 1.42 | 1.40 | 1.75 | 1.56 | 1.63 |
| | 0.52 | 0.47 | 0.48 | 0.44 | 0.50 | 0.45 | 0.44 | 0.45 | 0.55 | 0.49 | 0.52 |
| 2 | 49.85 | 49.49 | 49.22 | 49.10 | 48.78 | 48.36 | 47.82 | 47.88 | 49.01 | 48.12 | 47.42 |
| | 1.92 | 1.87 | 1.99 | 1.82 | 1.98 | 1.98 | 1.94 | 2.27 | 2.24 | 2.52 | 2.25 |
| | 0.61 | 0.59 | 0.63 | 0.58 | 0.63 | 0.63 | 0.61 | 0.72 | 0.71 | 0.80 | 0.71 |
| 3 | 48.52 | 46.93 | 44.51 | 43.32 | 43.19 | 42.98 | 42.43 | 42.83 | 42.81 | 41.85 | 41.62 |
| | 1.95 | 2.04 | 2.30 | 1.94 | 2.27 | 2.23 | 2.60 | 2.60 | 2.46 | 2.55 | 2.62 |
| | 0.62 | 0.64 | 0.73 | 0.61 | 0.72 | 0.70 | 0.82 | 0.82 | 0.78 | 0.81 | 0.83 |
| 4 | 48.51 | 46.56 | 43.33 | 41.88 | 40.58 | 40.60 | 39.53 | 40.05 | 40.08 | 39.28 | 38.90 |
| | 1.85 | 1.79 | 1.68 | 1.63 | 2.37 | 2.28 | 2.18 | 2.25 | 2.64 | 2.70 | 2.55 |
| | 0.58 | 0.57 | 0.53 | 0.52 | 0.79 | 0.76 | 0.73 | 0.75 | 0.88 | 0.90 | 0.85 |
| 5 | 49.06 | 46.95 | 43.85 | 44.68 | 44.75 | 44.43 | 44.02 | 44.72 | 45.20 | 44.53 | 44.49 |
| | 3.11 | 2.64 | 2.93 | 2.71 | 2.71 | 2.73 | 2.56 | 2.70 | 2.65 | 2.50 | 2.49 |
| | 0.98 | 0.84 | 0.93 | 0.86 | 0.86 | 0.86 | 0.81 | 0.85 | 0.84 | 0.79 | 0.79 |

Effect of Test Formulations on Feed Intake in db/db Mice:

db/db mice had significantly higher feed intake as compared to normal mice. Semaglutide API at 0.06 and 0.4 mg/kg/day doses showed significant reduction in daily feed intake as compared to vehicle control. Semaglutide depot at 25 mg/kg (dose 2 mg/kg, API based), IM, once on Day-1 only, showed significant reduction in daily feed intake as compared to vehicle control. The results are shown in FIGS. 9A-9D and summarized in Table 9.

TABLE 9

| | Mean feed intake (upper row); SD (middle row); SEM (bottom row) [g/cage/day] | | | | | | | |
|---|---|---|---|---|---|---|---|---|
| Group | Day 1 | Day 3 | Day 6 | Day 9 | Day 12 | Day 15 | Day 18 | Day 21 | Day 24 |
| 1 | 11.22 | 10.64 | 10.38 | 9.38 | 9.57 | 9.16 | 9.75 | 8.76 | 9.45 |
| | 1.40 | 1.36 | 1.16 | 1.15 | 0.69 | 0.87 | 0.94 | 1.46 | 2.86 |
| | 0.63 | 0.61 | 0.52 | 0.51 | 0.31 | 0.39 | 0.42 | 0.65 | 1.28 |
| 2 | 14.17 | 14.20 | 16.26 | 15.59 | 16.19 | 16.10 | 15.06 | 15.11 | 16.41 |
| | 2.18 | 1.32 | 1.62 | 4.22 | 2.28 | 2.55 | 0.37 | 0.85 | 1.40 |
| | 0.98 | 0.59 | 0.72 | 1.89 | 1.02 | 1.14 | 0.16 | 0.38 | 0.63 |
| 3 | 6.80 | 5.79 | 10.54 | 11.39 | 10.36 | 11.79 | 12.29 | 8.76 | 12.52 |
| | 1.26 | 3.38 | 3.74 | 4.63 | 0.95 | 3.15 | 1.83 | 2.39 | 1.97 |
| | 0.56 | 1.51 | 1.67 | 2.07 | 0.42 | 1.41 | 0.82 | 1.07 | 0.88 |
| 4 | 4.76 | 2.06 | 7.04 | 8.36 | 8.11 | 8.69 | 8.99 | 7.59 | 8.73 |
| | 1.13 | 1.50 | 0.85 | 2.25 | 0.61 | 0.37 | 0.68 | 2.21 | 3.32 |
| | 0.50 | 0.67 | 0.38 | 1.01 | 0.27 | 0.30 | 0.99 | 1.49 | |
| 5 | 4.46 | 6.85 | 10.05 | 12.13 | 9.76 | 10.08 | 11.52 | 11.52 | 12.22 |
| | 1.14 | 3.09 | 1.89 | 1.74 | 1.04 | 0.73 | 1.65 | 1.56 | 2.55 |
| | 0.51 | 1.38 | 0.84 | 0.78 | 0.46 | 0.33 | 0.74 | 0.70 | 1.14 |

Plasma Concentrations of Semaglutide Formulations in db/db Mice:

Plasma concentrations at Day 1 (0 h) were below limit of quantification, i.e. <10.2. Semaglutide API at 0.06 mg/kg/day, SC dose, administered daily showed an increase in plasma levels at 3 hrs post injection. Semaglutide API at 0.06 mg/kg/day, SC dose, administered daily showed ~100-500 ng/ml plasma levels 24 hrs post treatment. Semaglutide API at 0.4 mg/kg/day, SC dose administered daily showed an increase in plasma levels 3 hrs post injection. Semaglutide API at 0.4 mg/kg/day, SC dose, administered daily showed ~500-4,500 ng/ml plasma levels 24 h post treatment. This increase in plasma levels observed was dose proportional between 0.06 and 0.4 mg/kg doses.

Semaglutide depot at 25 mg/kg (dose 2 mg/kg, API based), IM, once on Day-1 only, showed declining plasma levels from Day-1 to Day-35. The results are shown in FIGS. 10A-10D and summarized in Tables 10A-10C.

TABLE 10A

Plasma concentrations (ng/ml)-Semaglutide API, 0.06 mg/kg, SC, Daily, n = 10

| Animal No. | Day 1 (3 h) | Day 7 (0 h) | Day 7 (3 h) | Day 14 (0 h) | Day 14 (3 h) | Day 21 (0 h) | Day 21 (3 h) | Day 28 (0 h) | Day 28 (3 h) |
|---|---|---|---|---|---|---|---|---|---|
| 1 | 318 | 389 | 1010 | 274 | 388 | 358 | 1110 | 391 | 617 |
| 2 | 475 | 152 | 1030 | 179 | 233 | 200 | 1100 | 529 | 823 |
| 3 | 236 | 206 | 1090 | 129 | 295 | 254 | 867 | 257 | 406 |
| 4 | 163 | 192 | 839 | 116 | 476 | 168 | 1190 | 322 | 483 |
| 5 | 227 | 248 | 888 | 180 | 471 | 213 | 806 | 242 | 474 |
| 6 | 312 | 175 | 1110 | 111 | 616 | 171 | 881 | 259 | 354 |
| 7 | 428 | 462 | 852 | 154 | 732 | 268 | 783 | 349 | 468 |
| 8 | 376 | 133 | 855 | 88.4 | 503 | 61.1 | 1220 | 370 | 946 |
| 9 | 301 | 205 | 726 | 118 | 304 | 269 | 629 | 232 | 410 |
| 10 | 230 | 272 | 767 | 169 | 703 | 237 | 827 | 320 | 501 |
| Mean | 306.6 | 243.4 | 916.7 | 151.84 | 472.1 | 219.91 | 941.3 | 327.1 | 548.2 |
| SD | 97.7 | 105.7 | 134.4 | 53.12 | 172.05 | 78.88 | 198.97 | 90.11 | 192.63 |
| SEM | 30.90 | 33.43 | 42.50 | 16.80 | 54.41 | 24.94 | 62.92 | 28.50 | 60.91 |

TABLE 10B

Plasma concentrations (ng/ml)-Semaglutide API, 0.4 mg/kg, SC, Daily, n = 10

| Animal No. | Day 1 (3 h) | Day 7 (0 h) | Day 7 (3 h) | Day 14 (0 h) | Day 14 (3 h) | Day 21 (0 h) | Day 21 (3 h) | Day 28 (0 h) | Day 28 (3 h) |
|---|---|---|---|---|---|---|---|---|---|
| 1 | 3430 | 2730 | 5490 | 2060 | 7290 | 2550 | 7820 | 1760 | 4900 |
| 2 | 4370 | 2600 | 6830 | 1780 | 6660 | 2810 | 7340 | 1460 | 3690 |
| 3 | 1310 | 1540 | 6440 | | | Animal died | | | |
| 4 | 1740 | 3730 | 4320 | 3110 | 9320 | 2340 | 6610 | 2940 | 6750 |
| 5 | 2000 | 1660 | 7910 | 1210 | 8690 | 2200 | 5830 | 1460 | 5780 |
| 6 | 1090 | 1000 | 3300 | 822 | 6870 | 2970 | 4870 | 2910 | 2920 |
| 7 | 852 | 1190 | 3100 | 733 | 3040 | 3720 | 2990 | 3340 | 3400 |
| 8 | 733 | 2010 | 5340 | 1480 | 6520 | 3020 | 3550 | 3530 | 4100 |
| 9 | 701 | 1920 | 3590 | 1140 | 2750 | 2530 | 3140 | 2880 | 6070 |
| 10 | 1320 | 2100 | 3370 | 1030 | 6500 | 2590 | 4090 | 4570 | 6690 |
| Mean | 1754.6 | 2048 | 4969 | 1485 | 6404.4 | 2747.8 | 5137.3 | 2761.1 | 4922.2 |
| SD | 1224.9 | 807.1 | 1694.6 | 747.1 | 2221.7 | 454.2 | 1836.6 | 1040.1 | 1459.5 |
| SEM | 387.36 | 255.22 | 535.87 | 249.03 | 740.56 | 151.40 | 612.21 | 346.70 | 486.48 |

TABLE 10C

Plasma concentrations (ng/ml)-Semaglutide depot (2 mg/kg, API based), 25 mg/kg, once on Day-1 only, IM, n = 10

| Animal No. | Day 1 (3 h) | Day 7 | Day 14 | Day 21 | Day 28 | Day 35 | Day 42 |
|---|---|---|---|---|---|---|---|
| 1 | 1370 | 171 | 42.4 | 52.1 | 121 | 57.8 | BLQ |
| 2 | 909 | 110 | 24.6 | 41.6 | 85.9 | 107 | 36.8 |
| 3 | 1010 | 149 | BLQ | BLQ | 23.1 | 103 | BLQ |
| 4 | 885 | 150 | BLQ | 13.7 | BLQ | 49.1 | BLQ |
| 5 | 1080 | 75.6 | 17.1 | BLQ | 49.7 | 51.6 | BLQ |
| 6 | 1230 | 109 | BLQ | BLQ | 72.6 | 20.8 | 12.4 |
| 7 | 1660 | 95 | 104 | 25.8 | 10.5 | 31.8 | BLQ |
| 8 | 952 | 70.8 | 59.3 | 15.6 | BLQ | 48.6 | 29.8 |
| 9 | 1020 | 38.3 | 55.9 | 11.1 | 111 | 54.5 | BLQ |
| 10 | 1210 | 198 | BLQ | 11.3 | BLQ | 43.2 | BLQ |
| Mean | 1132.60 | 116.67 | 50.55 | 24.46 | 67.69 | 56.74 | 26.33 |

TABLE 10C-continued

Plasma concentrations (ng/ml)-Semaglutide depot (2 mg/kg, API based), 25 mg/kg, once on Day-1 only, IM, n = 10

| Animal No. | Day 1 (3 h) | Day 7 | Day 14 | Day 21 | Day 28 | Day 35 | Day 42 |
|---|---|---|---|---|---|---|---|
| SD | 241.38 | 49.70 | 31.05 | 16.36 | 42.14 | 27.73 | 12.56 |
| SEM | 76.33 | 15.72 | 12.68 | 6.18 | 15.93 | 10.48 | 4.75 |

BLQ < 10.2

Thus, the depot compositions of the present invention maintain therapeutic plasma concentrations of semaglutide for at least 35 days after a single administration.

Example 5: Pharmacokinetic Study of Semaglutide Formulations in Mini-Pigs

Figure 11:
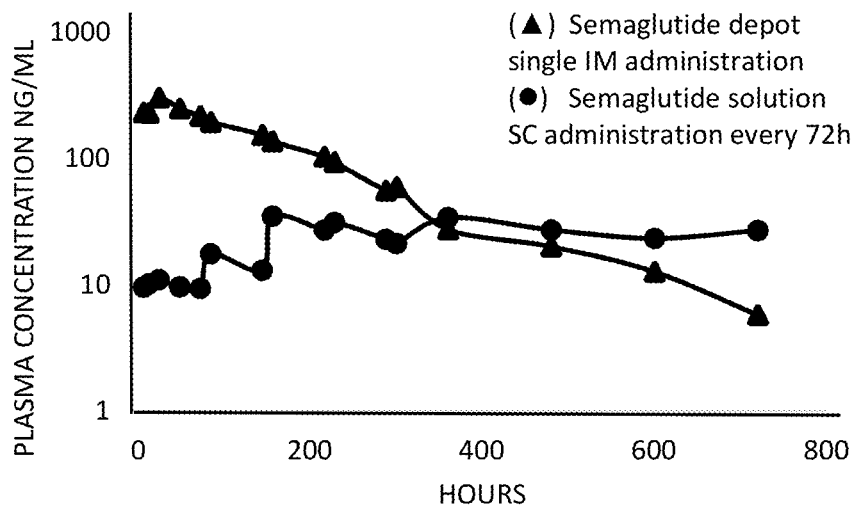
FIG. 11: shows semaglutide mean plasma concentrations in mini pigs. Semaglutide depot following a single IM administration (▲) vs. semaglutide solution administered subcutaneously every 72 h (●).

The objective of this study was to test the pharmacokinetic effect of various formulations of semaglutide in male Gottingen minipigs.
Treatment Groups:
 1. Semaglutide depot (SEMA-031120, 79 mg semaglutide/g MPs) dose 125 mg depot (10 mg/animal semaglutide based)/0.5 mL, IM on Day 0 (n=3)
 2. Semaglutide API dose 2 nmol/kg (0.008 mg/kg), SC, administered every 3 days until Day 28 (n=3)
Study Protocol:
 Blood Collection and Sample Storage
 Blood samples were collected through jugular vein from minipigs of Group 1 (IM) at—0, 6, 12, 24, 48, 72, 84, 144, 156, 216, 228, 288, 300, 360, 480, 600, 720 h (Day 30), Day 40, Day 50 and Day 60 post-dose (Total 20 time points/minipig) and of Group 2 (SC) at—0, 6, 12, 24, 48, 72 h (pre-administration), 84, 144 h (pre-administration), 156, 216 h (pre-administration), 228, 288 h (pre-administration), 300, 360 h (pre-administration), 480 h (pre-administration), 600 h (pre-administration), 720 h (Day 30) post-dose (Total 17 time points/minipig). At each time point, ~2.0 ml of blood was withdrawn and transferred into a prelabeled K$_2$EDTA coated vacutainers and mixed gently by inverting the tube to facilitate mixing of anticoagulant with the blood. Blood samples were kept on gel packs until centrifugation. The collected blood samples were centrifuged at 4,000 rpm for 10 min at 4° C. Plasma was separated after centrifugation. All plasma samples were transferred into pre-labeled (Animal ID No., Time point, Study No., and Group) tubes and stored at −70±10° C. until analysis. Blood glucose levels were determined for all blood collection time points.
 Bioanalysis
 Bioanalysis was performed using fit-for-purpose liquid chromatography mass spectrometry (LC-MS/MS) method for the quantification of semaglutide in plasma samples. Linearity range was 1 to 204 ng/ml. Semaglutide were extracted from mini pig plasma samples using solid phase extraction technique and quantified using LC-MS/MS with Electro Spray Ionization (ESI) and multiple reaction monitoring (MRM) in positive ionization mode.
 Pharmacokinetic Analysis
 The plasma pharmacokinetic parameters for semaglutide were calculated using standard non-compartmental analysis (Phoenix® software, version 8.3, Pharsight Corporation, Mountain View, California 94040/USA) using linear trapezoidal method with linear interpolation.
Results:
 No clinical signs and no mortality/morbidity were observed in the treated groups. The plasma pharmacokinetic parameters of semaglutide in male Gottingen minipigs were evaluated for the groups treated with a single IM (10 mg/animal) semaglutide depot administration and repeated SC (0.008 mg/kg, every 3 days until Day 28) semaglutide API administrations. Values are expressed as Mean ±SD and n=3 minipigs/time point/group. The mean±SD plasma concentrations–time profile of semaglutide are shown in FIG. 11 and summarized in Table 11. The corresponding pharmacokinetic parameters are summarized in Table 12.

TABLE 11

Mean plasma concentrations of semaglutide following a single IM or repeated SC administrations to male Gottingen minipigs

| Time (h) | Group 1 - Semaglutide depot | | Group 2 - Semaglutide API | |
|---|---|---|---|---|
| | Mean | SD | Mean | SD |
| 0 | 0 | 0 | 0 | 0 |
| 6 | 232.33 | 98.40 | 9.64 | 0.18 |
| 12 | 230.33 | 107.27 | 10.21 | 1.55 |
| 24 | 303.33 | 128.5 | 10.98 | 3.26 |
| 48 | 250.00 | 77.44 | 9.67 | 3.36 |
| 72 | 216.67 | 83.39 | 9.43 | 0.64 |
| 84 | 195.33 | 79.56 | 17.73 | 2.51 |
| 144 | 154.23 | 60.52 | 13.09 | 5.43 |
| 156 | 137.43 | 51.03 | 35.03 | 15.21 |
| 216 | 103.97 | 48.50 | 27.30 | 15.58 |
| 228 | 93.93 | 50.42 | 31.33 | 11.29 |
| 288 | 56.03 | 21.26 | 22.96 | 13.37 |
| 300 | 59.70 | 26.52 | 21.30 | 3.41 |
| 360 | 27.53 | 4.07 | 34.05 | 36.73 |
| 480 (For G1)/ 504 (For G2) | 20.10 | 13.68 | 27.33 | 1.90 |
| 600 (For G1)/ 648 (For G2) | 12.70 | 10.96 | 23.37 | 6.15 |
| 720 (Day 30) | 5.78 | 3.01 | 26.97 | 6.51 |
| 960 (Day 40) | 0 | 0 | NA | NA |
| 1,200 (Day 50) | 0 | 0 | NA | NA |
| 1,440 (Day 60) | 0 | 0 | NA | NA |

TABLE 12

Plasma pharmacokinetic parameters of semaglutide following a single IM or repeated SC administrations to male Gottingen minipigs

| PK parameters | Group 1 - Semaglutide depot | Group 2 - Semaglutide API |
|---|---|---|
| C$_{max}$ (ng/mL) | 303 ± 129 | 12.6 ± 1.21 |
| T$_{max}$ (hours)* | 24 | 24 (12–48) |
| AUC$_{0-72\,h}$ (h · ng/mL) | 17,500 ± 6,430 | 693 ± 53.6 |
| AUC$_{last}$ (h · ng/mL) | 54,400 ± 19,200 | 17,600 ± 5,440 |
| AUC$_{inf\_obs}$ (h · ng/mL) | 55,500 ± 19,500 | Not calculated** |
| AUC $_{\%\,Extrap\_obs}$ (%) | 1.98 ± 1.00 | Not calculated** |
| K$_{el}$ (1/h) | 0.0058 ± 0.00101 | Not calculated** |
| T$_{1/2}$ (h) | 122 ± 20.2 | Not calculated** |
| Cl/F__obs (mL/min/kg) | 39 ± 67.2 | Not calculated** |
| Vz/F__obs (L/kg) | 473 ± 816 | Not calculated** |
| MRT$_{last}$ (h) | 164 ± 24.5 | Not calculated** |

*expressed as Median (Minimum-Maximum)
**value of % AUC$_{exp}$ >25% and R$_{sq}$ value <0.8

In Group 1 (Semaglutide depot: 10 mg/animal, a single IM injection), the median time to reach peak plasma concentration (T$_{max}$) was 24 h and a peak plasma concentration (C$_{max}$) of 303±129 ng/mL with a terminal half-life (T$_{1/2}$) of 122±20.2 h were obtained. The mean exposures, AUC$_{last}$ and AUC$_{inf}$ were found to be 54,400±19,200 and 55,500±19,500 ng*hr/mL, respectively.

In Group 2 (Semaglutide API: 0.008 mg/kg, repeated SC injections), the time to reach mean peak plasma concentration (T$_{max}$) was 24 h (12–48) and a peak plasma concentration ($C_{max}$) of 12.6±1.21 ng/mL was obtained. The mean exposure ($AUC_{last}$) was found to be 17,600±5,440 ng*hr/mL.

The study shows that a single intramuscular administration of a depot semaglutide formulation according to certain embodiments of the present invention affords effective plasma concentrations of over a month following administration.

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

The invention claimed is:

1. A long-acting parenteral pharmaceutical composition comprising dried microparticles comprising a therapeutically effective amount of semaglutide or a pharmaceutically acceptable salt thereof and a biodegradable carrier at a ratio of about 1:10 to about 1:15 (w/w),
   wherein the composition releases less than 20% of semaglutide or a pharmaceutically acceptable salt thereof over 24 hours in a phosphate buffer at pH 7.4,
   wherein the composition releases less than 80% of the semaglutide or pharmaceutically acceptable salt thereof over 14 days in a phosphate buffer at pH 7.4,
   wherein the composition releases more than 80% of the semaglutide or pharmaceutically acceptable salt thereof over 28 days in a phosphate buffer at pH 7.4,
   wherein semaglutide is released from the composition in a continuous manner over 14 days upon dissolution in a phosphate buffer at pH 7.4,
   wherein the composition releases the semiglutide active ingredient over a period of about four weeks to about two months,
   wherein the long-acting parenteral pharmaceutical composition is a long-acting depot composition suitable for administration at a medically acceptable location in a subject in need thereof at a frequency of once every four weeks to once every six months, and
   wherein the dried microparticles are formed by drying water-in-oil-in-water (w/o/w) double emulsion droplets comprising:
   a) an internal aqueous phase comprising a therapeutically effective amount of semaglutide or a pharmaceutically acceptable salt thereof;
   b) a water immiscible polymeric phase comprising a biodegradable carrier selected from the group consisting of polylactides, polyglycolides, polycaprolactones, and combinations thereof, and a first surfactant comprising a fatty acid or a derivative thereof; and
   c) an external aqueous phase comprising a tonicity modifier comprising sodium chloride,
   wherein the dried microparticles are devoid of any coating layer.

2. The long-acting parenteral pharmaceutical composition of claim 1, wherein semaglutide is released from the composition at a first order controlled release.

3. The long-acting parenteral pharmaceutical composition of claim 1 comprising semaglutide or a pharmaceutically acceptable salt thereof as the sole active ingredient.

4. The long-acting parenteral pharmaceutical composition of claim 1, wherein at least one of the internal and external aqueous phases further comprises a second surfactant.

5. The long-acting parenteral pharmaceutical composition of claim 4, wherein the second surfactant is selected from the group consisting of polyvinyl alcohol (PVA), polysorbate, polyethylene oxide-polypropylene oxide block copolymers, polyethylene glycol, and cellulose esters.

6. The long-acting parenteral pharmaceutical composition of claim 1, wherein the biodegradable carrier is a polymer selected from the group consisting of poly (D,L-lactide-co-glycolide) (PLGA), poly (D,L-lactide) (PLA), polyglycolide (PGA), polycaproactone (PCL), and combinations thereof.

7. The long-acting parenteral pharmaceutical composition of claim 6, wherein the biodegradable carrier is poly (D,L-lactide-co-glycolide) (PLGA).

8. The long-acting parenteral pharmaceutical composition of claim 1, wherein the first surfactant comprising a fatty acid or a derivative thereof is lecithin, hydrogenated lecithin, stearic acid, or a mixture of combination thereof.

9. The long-acting parenteral pharmaceutical composition of claim 4, wherein the water-in-oil-in-water (w/o/w) double emulsion droplets are formed by a process comprising the steps of:
   (i) dispersing an aqueous suspension or solution of semaglutide or a pharmaceutically acceptable salt thereof in a solution of a biodegradable carrier and the first surfactant in a water-immiscible volatile organic solvent, thereby obtaining a water-in-oil emulsion; and
   (ii) dispersing said water-in-oil emulsion in a continuous external water phase comprising the second surfactant and the tonicity modifier, to form microparticles comprising water-in-oil-in-water (w/o/w) double emulsion droplets.

10. The long-acting parenteral pharmaceutical composition of claim 9, wherein the process further comprises the step of (iii) collecting the thus formed microparticles by filtration or centrifugation.

11. The long-acting parenteral pharmaceutical composition of claim 10, wherein the process further comprises the step of (iv) washing the collected microparticles.

12. The long-acting parenteral pharmaceutical composition of claim 11, wherein the process further comprises the step of drying the collected or washed microparticles.

13. A composition comprising the long-acting parenteral pharmaceutical composition of claim 1, reconstituted in a physiologically acceptable solvent.

14. A method of treating type-2 diabetes mellitus, comprising the step of administering to a subject in need thereof the long-acting parenteral pharmaceutical composition of claim 1 at a frequency of once every four weeks to once every six months.

15. The method of claim 14, wherein treating type-2 diabetes mellitus comprises reducing fasting glucose levels in a subject by at least about 5% for a time period between about four weeks and about six months after a single administration; or wherein treating type-2 diabetes mellitus comprises reducing fed glucose levels in a subject by at least about 5% for a time period between about four weeks and about six months after a single administration; or wherein treating type-2 diabetes mellitus comprises reducing hemoglobin A1c (HbA1c) levels in a subject by at least about 5% for a time period between about four weeks and about six months after a single administration.

16. A method of treating obesity comprising the step of administering to a subject in need thereof the long-acting parenteral pharmaceutical composition of claim 1 at a frequency of once every four weeks to once every six months.

17. A method of treating Parkinson's Disease, comprising the step of administering to a subject in need thereof the long-acting parenteral pharmaceutical composition of claim 1 at a frequency of once every four weeks to once every six months.

18. The long-acting parenteral pharmaceutical composition of claim 1, wherein the composition releases the semaglutide active ingredient over a period of about four weeks to about six weeks.

19. The long-acting parenteral pharmaceutical composition of claim 11, wherein washing the collected microparticles is performed with an aqueous solution comprising divalent cations.

\* \* \* \* \*